(12) United States Patent
Bayer et al.

(10) Patent No.: US 10,478,562 B2
(45) Date of Patent: Nov. 19, 2019

(54) DRIVE MECHANISM OF A DRUG DELIVERY DEVICE

(71) Applicant: Sanofi, Paris (FR)

(72) Inventors: Stefan Bayer, Würselen (DE); Daniel Berning, Baesweiler (DE); Philippe Blank, Düsseldorf (DE); Wolfgang Pelzer, Kreuzau (DE); Björn Wilden, Simmerath (DE)

(73) Assignee: Sanofi, Paris (FR)

( * ) Notice: Subject to any disclaimer, the term of this patent is extended or adjusted under 35 U.S.C. 154(b) by 690 days.

(21) Appl. No.: 14/782,622

(22) PCT Filed: Apr. 8, 2014

(86) PCT No.: PCT/EP2014/056983
§ 371 (c)(1),
(2) Date: Oct. 6, 2015

(87) PCT Pub. No.: WO2014/166905
PCT Pub. Date: Oct. 16, 2014

(65) Prior Publication Data
US 2016/0045663 A1 Feb. 18, 2016

(30) Foreign Application Priority Data

Apr. 10, 2013 (EP) ..................... 13163082

(51) Int. Cl.
*A61M 5/315* (2006.01)
*A61M 5/20* (2006.01)
(Continued)

(52) U.S. Cl.
CPC ............. *A61M 5/315* (2013.01); *A61M 5/20* (2013.01); *A61M 5/31511* (2013.01);
(Continued)

(58) Field of Classification Search
CPC .......... A61M 15/0045; A61M 5/31553; A61M 15/0065; A61M 3/31583; A61M 5/31593;
(Continued)

(56) References Cited

U.S. PATENT DOCUMENTS 5,697,916 A * 12/1997 Schraga .............. A61M 5/1782
604/155
5,947,934 A * 9/1999 Hansen ............. A61M 5/31525
604/187
(Continued)

FOREIGN PATENT DOCUMENTS

CN 1374876 10/2002
CN 102596291 7/2012
(Continued)

OTHER PUBLICATIONS

Rote Liste, "50. Hypophysen-, Hypothalamushormone, andere regulatorische Peptide u. ihre Hemmstoffe," Chapter 50, ed. 2008, 20 pages.
(Continued)

*Primary Examiner* — Laura A Bouchelle
*Assistant Examiner* — Dung T Ulsh
(74) *Attorney, Agent, or Firm* — Fish & Richardson P.C.

(57) ABSTRACT

A drive mechanism of a drug delivery device for setting and dispensing of a dose of a medicament includes a housing, a piston rod, a dose indicating member with a dose size information thereon, and a drive wheel. The piston rod engages with a piston of a cartridge for displacing the piston in a distal direction. The dose indicating member is connected to a spring element and is rotatable in a dose incrementing direction against the action of the spring element for setting a dose. The drive wheel is operably engaged with the piston rod for displacing the piston rod in the distal direction for dose dispensing. The dose indicating
(Continued)

member is engageable with the drive wheel during dose dispensing to transfer a force to the drive wheel when driven by the relaxing spring element in a dose decrementing direction.

20 Claims, 14 Drawing Sheets

(51) Int. Cl.
*A61M 5/24* (2006.01)
*A61M 5/31* (2006.01)

(52) U.S. Cl.
CPC .... *A61M 5/31533* (2013.01); *A61M 5/31541* (2013.01); *A61M 5/31553* (2013.01); *A61M 5/31583* (2013.01); *A61M 5/24* (2013.01); *A61M 5/31593* (2013.01); *A61M 2005/3126* (2013.01)

(58) Field of Classification Search
CPC .......... A61M 15/0003; A61M 15/0068; A61M 5/315; A61M 5/20; A61M 5/31511; A61M 5/31533; A61M 5/31541; A61M 5/31583; A61M 5/24; A61M 2005/3126
USPC .......... 604/71, 186, 207, 208, 211, 224, 246
See application file for complete search history.

(56) References Cited

U.S. PATENT DOCUMENTS

| | | | | |
|---|---|---|---|---|
| 6,582,404 | B1* | 6/2003 | Klitgaard | A61M 5/31511 604/181 |
| 8,876,766 | B2* | 11/2014 | Holmqvist | A61M 5/2033 604/135 |
| 2005/0090782 | A1* | 4/2005 | Marshall | A61M 5/31525 604/211 |
| 2006/0276753 | A1* | 12/2006 | Kronestedt | A61M 5/20 604/186 |
| 2006/0276754 | A1* | 12/2006 | Kronestedt | A61M 5/20 604/186 |
| 2009/0082727 | A1* | 3/2009 | Moeller | A61M 5/14224 604/132 |
| 2009/0245045 | A1* | 10/2009 | Doi | G11B 7/126 369/47.5 |
| 2011/0092905 | A1 | 4/2011 | Cowe | |
| 2012/0004639 | A1* | 1/2012 | Schoonmaker | A61M 5/204 604/506 |
| 2013/0041322 | A1* | 2/2013 | Holmqvist | A61M 5/31525 604/189 |
| 2013/0296778 | A1* | 11/2013 | Damgaard-Soerensen | A61M 5/2448 604/82 |

FOREIGN PATENT DOCUMENTS

| | | |
|---|---|---|
| CN | 102639173 | 8/2012 |
| EP | 0 525 525 | 2/1993 |
| JP | K2008-504919 | 2/2008 |
| JP | 2009-050713 | 3/2009 |
| JP | K2013-506447 | 2/2013 |
| WO | WO 2001/019434 | 3/2001 |
| WO | WO 2002/092153 | 11/2002 |
| WO | WO 2011/039203 | 6/2011 |

OTHER PUBLICATIONS

International Preliminary Report on Patentability International Application No. PCT/EP2014/056983, dated Oct. 13, 2015, 8 pages.
International Search Report and Written Opinion in International Application No. PCT/EP2014/056983, dated Sep. 16, 2014, 12 pages.

* cited by examiner

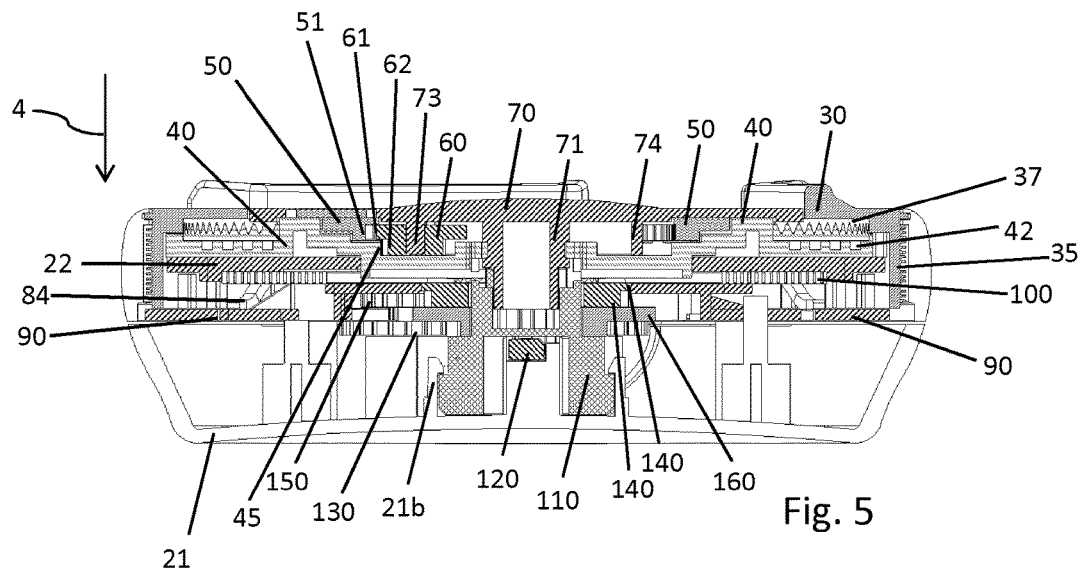

DRIVE MECHANISM OF A DRUG DELIVERY DEVICE

This application is a § 371 U.S. National Stage Application of PCT/EP2014/056983, filed Apr. 8, 2014, which claims priority to European Patent Application 13163082.4, filed Apr. 10, 2013, the entire contents of which are incorporated herein by reference.

The present invention relates to a drive mechanism for a drug delivery device and to a respective drug delivery device. In particular, the invention relates to an injection device such like a pen-type injector inter alia comprising a single and/or a last-dose limiting mechanism and further comprising a comparatively large dose indicating display.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

With such multi-dose drug delivery devices at least a last dose limiting mechanism is required to inhibit setting of a dose exceeding the amount of medicament left in the cartridge. This is to avoid a potentially dangerous situation for the user believing that a set dose is or will be entirely injected.

Drug delivery devices such like pen type injectors also provide a dose indicating mechanism which is operable to display the size of a set dose to a user. Typically, the housing of such drug delivery devices comprises a dose indicating window where a number representing the size of the dose shows up.

Especially with elderly or visually impaired patients, reading of such dose indicating numbers is sometimes difficult. With devices adapted for injection of e.g. insulin, typical dose sizes may vary between 0 and 120 IU (International Units) of insulin. Due to the rather compact design and limited geometrical dimensions of such drug delivery devices the size of such dose indicating numbers is fairly small. For visually impaired persons reading of such tiny numbers may therefore be rather difficult. However, since such drug delivery devices are intended for self-medication treatment, it is of importance, that the user is able to correctly determine the size of dose actually set.

OBJECTS OF THE INVENTION

It is therefore an object of the present invention to avoid disadvantages of known drug delivery devices and to provide a drive mechanism of a drug delivery device allowing for an intuitive operation, both for setting and for dispensing of a dose. It is another object to provide a dose indicating mechanism which is easy and unequivocal to read even for persons suffering impaired vision.

In another object, the invention serves to provide a drive mechanism of a drug delivery device for setting and dispensing of a dose of a medicament and further featuring a single and/or a last dose limiting mechanism.

It is a further aim to provide a drug delivery device comprising such a drive mechanism and comprising a cartridge sealed with a piston and being operably engaged with a piston rod of such drive mechanism.

SUMMARY OF THE INVENTION

In a first aspect a drive mechanism for a drug delivery device is provided for dispensing of a dose of a medicament. The drive mechanism comprises a substantially elongated housing, e.g. extending in a distal direction. The housing may be at least in sections of substantially tubular or cylindrical shape that allows gripping and operating of the drive mechanism or of the entire drug delivery device by one hand of a user. The housing may also comprise a bulged, almost circular shaped, disc like portion, e.g. at a proximal end which may smoothly fit into a palm of a user's hand.

The drive mechanism further comprises a piston rod to operably engage with a piston of a cartridge containing the medicament to be dispensed by the drive mechanism. The cartridge comprises a piston, which by means of a displacement in distal direction, serves to expel an amount of the medicament from the cartridge that corresponds to the distal displacement of the piston. The piston typically seals the cartridge in proximal direction. The piston rod serves to displace the piston of the cartridge in a distal direction. The piston rod is therefore operable to apply distally directed thrust or pressure to the piston of the cartridge for displacing the same in distal direction for a predetermined distance that corresponds to a respective amount of the medicament to be dispensed and which may therefore be expelled from the cartridge.

The drive mechanism further comprises a dose indicating member with dose size information thereon. Dose size information is typically represented by consecutive numbers, e.g. representing international units of insulin. The dose indicating member is connected to a spring element and it is further rotatable in a dose incrementing direction relative to the housing against the action of the spring element. By rotating the dose indicating member against the action of the spring element, the spring element can be strained and respective mechanical energy can be stored by the spring element. Typically, the dose indicating member is rotatable in dose incrementing direction for setting of a dose, hence during a dose setting procedure.

The drive mechanism further comprises a drive wheel operably engaged with the piston rod for displacing the piston rod in distal direction for dose dispensing. Typically, the drive wheel and the piston rod are permanently mechanically engaged. Drive wheel and piston rod may be threadedly engaged or may be rotatably locked. The piston rod may is typically guided by and in the housing.

The piston rod may for instance be threadedly engaged with the housing while the drive sleeve may be rotatably locked to the piston rod. A rotation of the drive wheel then may equally transfer into a respective rotation of the piston rod, thereby advancing the piston rod in distal direction due to its threaded engagement with the housing.

In other embodiments, the piston rod may be rotatably locked to the housing and may therefore be only translationally displaceable relative to the housing. Here, the drive wheel may be threadedly engaged with the piston rod so that a rotation of the drive wheel, which is secured and fixed with regard to the distal direction relative to the housing, is operable to induce a respective distally directed and translational but non-rotational displacement of the piston rod.

With other implementations, the mutual engagement of drive wheel and piston rod may comprise a rack and pinion assembly, wherein the drive wheel comprises a pinion or sprocket engaged with a rack portion of the piston rod. In this way, a rotation of the drive wheel can be directly transferred into a distally directed displacement of the piston rod.

Irrespective of the mutual engagement of drive wheel and piston rod, the dose indicating member operably connected with the spring element is engageable with the drive wheel during dose dispensing to transfer a driving force to the drive wheel, when the dose indicating member is driven by the relaxing spring element in a dose decrementing direction. It is in particular the dose indicating member itself that serves and acts as a drive member to transfer a relaxing force or relaxing action of the spring element into a driving torque, by way of which the semi-automated drive mechanism can be set in motion for displacing the piston rod in distal direction during dose dispensing.

In this way, the dose indicating member not only serves to display dose size related information to a user of the device but also acts as a driving component, by way of which mechanical energy transferred to and stored by the spring element can be transferred into the drive mechanism for setting in motion its various functional components during a dose dispensing procedure.

The dose indicating member and the drive wheel are typically selectively engageable for setting and dispensing of a dose. During a dose setting procedure, hence in dose setting mode, the dose indicating member is operably disconnected from the drive wheel. In this way, a dose of variable size can be set without any influence on the drive wheel and the piston rod. After setting of a dose and after the spring element has been strained or tensioned respectively, the drive mechanism can be switched into a dose dispensing mode, thereby operably engaging the dose indicating member and the drive wheel for that the mechanical energy previously stored by the spring element can be released and transferred to the dose indicating member, thereby inducing a respective driving force to the drive wheel and hence to the piston rod.

Typically, drive wheel and dose indicating member are indirectly engaged during dose dispensing. There may be provided at least one or a series of transmission gears or other functional components in the force transmitting path between dose indicating member and drive wheel in order to provide a required transmission ratio between the rotation of the dose indicating member and the rotation of the drive wheel during dose dispensing.

Typically, there is also provided a kind of a clutch assembly, by way of which the drive mechanism can be repeatedly and reversibly switched between the dose setting mode and the dose dispending mode, for setting and dispensing of a required dose, respectively.

Since the dose indicating member provides a double function, the total number of components the drive mechanism is made of can be reduced, thereby allowing for a rather compact and function-efficient design of the drive mechanism and the entire drug delivery device.

In another embodiment, the dose indicating member comprises a flat-shaped dose indicating disc. The dose indicating member or dose indicating disc typically comprises a circular geometry and may be rotatably supported in the housing with respect to its radial central portion. An axis of rotation of the dose indicating member may extend substantially perpendicular to the elongation of the piston rod, hence perpendicular to the elongation of the cartridge containing the medicament to be dispensed.

Moreover, the dose indicating member may be located in a correspondingly-shaped bulged or circular-shaped portion of the housing, typically located at a proximal end thereof to ergonomically fit in the palm of a user's hand. When the axis of rotation of the dose indicating member is oriented perpendicular or at a predefined angle with respect to the distal direction, the dose indicating member, hence the dose indicating disc may face towards a sidewall portion of the housing, e.g. featuring a comparatively large size compared to the diameter of a distally located cartridge holder portion of the housing, which is generally adapted to receive and to fix the tubular shaped cartridge filled with the medicament.

By arranging the dose indicating member towards or below a bulged sidewall portion of the housing, the overall size of the dose indicating member can be increased, thereby allowing to represent dose size information on a comparatively large scale. In this way, readability of the dose size information can be effectively increased, thus improving handling of the device especially for patients suffering impaired vision.

The dose size information is typically provided on a radial outer portion on a side face of the dose indicating disc. By making use of a radial outer section of the dose indicating disc, the overall space to be used as a number scale can be maximized. Typically, the dose indicating member is located beneath a dose indicating window, which may be provided in a respective housing portion effectively covering the dose indicating member.

The size of the dose indicating window typically fits with the size of the dose size information, e.g. with the size of consecutive numbers present on the dose indicating member. According to a momentary position or orientation of the dose indicating member relative to the dose indicating window, a respective number or dose size information visibly shows up in the dose indicating window thereby indicating to a user size information about size of the dose actually set.

The dose indicating mechanism provided by the dose indicating member may further comprise an additional, hence a second dose indicating member operably engaged with the dose indicating disc. The second dose indicating member may comprise a dose indicating ring or disc. Generally, respective first and second dose indicating members may be operable to illustrate various digits of a dose indicating number. While for instance the first dose indicating member may represent single units of the said dose, the second dose indicating disc may represent tens or decades of units, such like 10, 20, 30, 40, and so on. In this way, every number of a comparatively large dose size information, which may exceed even 100 IU, can be precisely displayed to a user or patient.

According to another embodiment, the spring element comprises a spiral spring having a first end section operably connected to the housing and having a second end section connected to the dose indicating member. The spiral spring is of substantially flat geometry. The spring element may extend in a common plane while only its opposite radially inwardly and radially outwardly located end sections are connected with the housing and with the dose indicating member, respectively. By implementing the dose indicating member in form of a flat shaped substantially planar disc and by making use of a planar spiral spring, a rather flat and overlapping configuration of mutually engaging dose indicating member and spring element can be attained.

It is to be noted here, that the overall geometry of the dose indicating disc and its surrounding housing portion defines the axial direction in the present context. Typically, the axial direction as further used extends substantially parallel or overlaps with the axis of rotation of the dose indicating member. The disc-shaped dose indicating member extends in radial direction and substantially overlaps with the interconnected spiral spring in axial direction. Regarding the overall geometry of the drug delivery device, the piston rod and hence the cartridge extend radially outwardly from the dose indicating member and/or a respective circular-shaped housing portion. Hence the distal direction extends substantially perpendicular to the axial direction.

According to a further embodiment, a ring-shaped dose setting member is provided, which is rotatably supported by or to the housing and which is selectively engageable with the dose indicating member for setting of a dose. Typically, the dose setting member is located in a sidewall portion of the housing of the drive mechanism. It may even form a sidewall portion of the housing of the drive mechanism. Accordingly, the sidewall portion of the housing may comprise a respective through opening, in which the ring-shaped dose setting member is rotatably supported.

Typically, the dose setting member is operably engageable with the dose indicating member during dose setting. The dose setting member is further operably disengageable from the dose indicating member during dose dispensing. In dose dispensing mode, the dose indicating member is driven in a dose decrementing direction, thereby illustrating respective dose size indicating numbers in a decrementing way through a dose indicating window.

Hence, during dose dispensing the dose indicating mechanism typically resets and may typically indicate a zero-dose size when a dose dispensing procedure terminates. The ring-shaped dose setting member may further be provided with at least one or several axially extending protruding portions, allowing an intuitive and easy gripping thereof. In this way, a user may easily grasp and grip the dose setting member for inducing a dose setting torque thereto during a dose setting procedure.

Respective axially outwardly extending gripping portions of the dose setting member may comprise a circumferentially and/or radially extending structure. Circumferentially or tangentially extending structures located on the dose setting member provide an effective gripping means, e.g. for a thumb and index finger of a user while radially extending sections of the gripping portion are adapted to receive and to transfer tangentially or circumferentially directed torque exerted by a user during dose setting.

The dose setting member may form an axial insert to be axially placed in the housing of the drive mechanism, thereby forming at least a portion of a circular-shaped sidewall portion thereof. In this way, the dose setting member can be aesthetically integrated into the outer appearance of the drive mechanism's housing.

In a further embodiment the drive mechanism also comprises a dose dispensing member rotatably fixed to the housing. The dose dispensing member is typically depressible in axial direction against the action of a spring element, typically denoted as dispensing spring element. Said dispensing spring element is to be biased and tensioned in axial direction and serves to keep and to displace the dose dispensing member into an initial configuration, which typically corresponds to the dose setting mode of the drive mechanism.

The dose dispensing member is typically splined to the housing, i.e. it is rotatably locked to the housing but may be axially displaceable relative to the housing. By means of depressing the dose dispensing member, e.g. in a downward or inward direction with regard to the geometry of the housing, the drive mechanism can be switched from the dose setting mode into the dose dispensing mode against the action of the dispensing spring element. Releasing of the dose dispensing member may then immediately return the same into its initial configuration. In the same way, the drive mechanism can be switched from the dose dispensing mode into the dose setting mode under the action of the dispensing spring element.

According to another embodiment the dose indicating member also axially abuts with the dose dispensing member. In this way, e.g. a downward directed axial displacement of the dose dispensing member can be equally transferred to the dose indicating member. Hence, the dose indicating member is also axially displaceable relative to the housing, in particular for switching the drive mechanism between dose dispensing and dose setting mode.

The dispensing spring element may be integrally formed with either the dose dispensing member or with the dose indicating member. Alternatively, the dispensing spring element may be provided as a separate piece or may be integrated into another functional component of the drive mechanism. It may be for instance integrated into a locking member, by way of which a rotation of the dose setting member can be blocked when the drive mechanism is in dose dispensing mode.

Typically, the dose indicating member is located underneath the dose dispensing member. It may then be of further benefit, when the dispensing spring element is located underneath or below the dose indicating member. In this way, a downward directed axial displacement of the dose dispensing member may equally transfer into a respective axially and downwardly directed displacement of the dose indicating member, thereby straining the dispensing spring element.

A release of the dose dispensing member, either prematurely to interrupt a dose dispensing procedure or at the end of a dose dispensing procedure may then lead to a respective upwardly directed displacement of both, the dose indicating member and the dose dispensing member in axial abutment therewith. In this way, a combined axial displacement of both, dose indicating member and dose dispensing member can be provided by means of a single dispensing spring element.

According to another embodiment, the dose dispensing member also comprises a through opening serving as a dose indicating window through which at least a portion of the dose size information of the dose indicating member is visibly displayed. The dose dispensing member may therefore at least partially cover an upward facing side face of the dose indicating member. Since dose dispensing member and dose indicating member are and remain in axial abutment, a respective axial displacement of the dose dispensing member for dispensing the dose has substantially no influence on the readability of the dose size information of the dose indicating member showing up in the dose indicating window of the dose dispensing member.

By providing the dose indicating window in or on the dose dispensing member, a rather intuitive and simple handling of the device can be provided. Hence, the patient simply has to depress a component of the drive mechanism, which at the same time also displays respective dose size information. Typically, the dose dispensing member itself provides a kind of a housing portion of the drive mechanism. It may serve as a closure of a respective through opening provided in the housing of the drive mechanism.

Typically, the dose dispensing member embodied as a depressible dose button is of rather disc-like shape in order to at least partially cover an information containing side face of the dose indicating member. Additionally, by providing a disc- or circular-shaped dose dispensing member, its thrust receiving surface, by way of which a user may interact with the dose dispensing member, can be designed comparatively large. In effect, the overall size of the dose dispensing member may become rather large, so that a user may easily depress the dose dispensing member, e.g. in form of a dose dispensing disc or button in a very intuitive and safe way.

According to another embodiment, the dose dispensing member is radially enclosed by the dose setting member. Hence, an upper side face of the housing of the drive mechanism may even in sections entirely consist of the concentric arrangement of dose setting member and dose dispensing member. Typically, the dose dispensing member of disc-like shape may completely fill the interior of the surrounding dose setting member. In this way, the complete functionality of the drive mechanism may be presented on one side of the housing.

A user may grasp the radially outwardly located dose setting member for setting of a dose and may then depress the radially inwardly located dose dispensing member into the housing for initiating a respective dose dispensing action of the drive mechanism. It is of particular benefit, when the outer or upper surface sections of dose dispensing member and dose setting member substantially flush in order to provide a rather aesthetic outer appearance to the drive mechanism's housing. Additionally, the dose dispensing member, e.g. the dose dispensing button may feature an axially bulged portion in its central region in order to haptically indicate to a user, where to depress the dose dispensing member.

By providing a dose dispensing member and a dose setting member in an interleaved and concentric way in a circular-shaped portion of the drive mechanism's housing, the housing itself does not have to provide a cover for the drive mechanism. Instead, the drive mechanism located inside the housing is covered by the arrangement of dose setting member and dose dispensing member, thereby reducing material and weight of the housing and of the respective drug delivery device.

In a further embodiment, the dose indicating member also comprises a spiralled groove or a comparable spiral shaped structure, on its upper or lower side face to engage with a single dose limiting member. Typically, the spiralled groove is located radially outwardly from the dose size information and is provided on either the same or on an opposite side face of the disc-shaped dose indicating member. Typically, during a dose incrementing rotation of the dose indicating member, the single dose limiting member travels along the spiralled groove thereof. The spiralled groove or some other functional component of the drive mechanism further provides a stop feature and blocks a further displacement of the single dose limiting member relative to said groove when a maximum dose size configuration has been reached.

In this way, the single dose limiting member provides a blocking of the dose indicating member and hence a blocking of the entire drive mechanism for not exceeding a maximum allowable dose size during dose setting. During dose dispensing, the dose indicating member is subject to a reverse, hence dose decrementing rotation. Accordingly, the single dose limiting member experiences a counter-directed displacement along the spiralled groove.

According to another embodiment, the single dose limiting member is radially displaceable relative to the dose dispensing member along the spiralled groove and it is rotatably fixed to the dose dispensing member. Alternatively, it may also be radially displaceable relative to the housing and may be rotatably fixed to the housing. By its radial displacement and rotatable engagement to the dose dispensing member, the single dose limiting member is effectively hindered to rotate together with the dose indicating member during dose setting and/or during dose dispensing. Due to its rotatable interlock relative to the dose dispensing member and/or relative to the housing, a dose incrementing or dose decrementing rotation of the dose indicating member leads to a respective displacement of the single dose limiting member along the spiralled groove.

The spiralled groove itself, the housing of the drive mechanism and/or the dose dispensing member may further comprise a radial stop to engage with a respective leading or trailing edge of the single dose limiting member. When getting in abutment with a respective stop, the single dose limiting member is hindered to travel further along the spiralled groove. Due to its rotational interlock to the rotatably fixed dose dispensing member or to the housing, any further rotational displacement of the dose indicating member and hence of the entire drive mechanism in dose incrementing direction can be effectively blocked.

Typically, such a blocking configuration is reached, when the dose indicating member or dose setting member has turned a predefined angular distance that corresponds to a maximum allowable dose size, e.g. 120 IU of insulin.

The single dose limiting member may not only provide a maximum limiter but also a minimum limiter in order to block a dose decrementing rotation of the dose indicating member at the end of a dose dispensing procedure. Accordingly, the dose limiting member may equally engage with a respective stop, in particular with a radially extending stop provided on the dose indicating member, e.g. at an opposite end of the spiralled groove. Alternatively, such a zero-dose stop may also be provided by the housing of the drive mechanism or by the dose dispensing member.

A zero-dose stop to engage with the single dose limiting member may provide a well defined end of the dispensing function so that the dose dispensing procedure terminates when the dose indicating member has reached its zero-dose configuration, in which e.g. a zero-dose number "0" shows up in the dose indicating window. This additional zero-dose stop therefore provides a well defined initial configuration for the drive mechanism at the end of a dose dispensing procedure and during dose setting.

Additionally, the zero-dose stop of the drive mechanism may audibly engage with the single dose limiting member. For instance, the single dose limiting member may feature a resiliently deformable clicking member to engage with a correspondingly-shaped clicking member provided near the zero-dose stop of e.g. the spiralled groove. In this way, an audible click sound can be generated at the end of a dispensing procedure, thereby indicating to a user or patient, that a dose dispensing action has just terminated or is about to end.

According to a further embodiment, the dose dispensing member comprises a radially outwardly extending appendix engaged with a notch of the single dose limiting member. The notch of the single dose limiting member is typically provided on an upper face of the single dose limiting member opposite to a lower portion thereof being in engagement with the spiralled groove of the dose indicating member. By means of the radially outwardly extending appendix engaging with the dose limiting member's notch, the single dose limiting member can be rotatably fixed or radially splined to the dose dispensing member. Since the dose dispensing member is also rotatably fixed to the housing, the single dose limiting member is also rotatably secured thereto via the dose dispensing member.

In a further embodiment, the dose setting member comprises a circumferential sidewall portion extending into the housing. Typically, the housing portion adapted to receive the dose setting member comprises a circumferentially or almost cylindrically extending sidewall to receive a correspondingly-shaped sidewall portion of the dose setting member. Hence, the housing and the dose setting member may comprise mutually corresponding sleeve-like shaped sidewall portions to form a radial gap therebetween when the dose setting member is assembled in or on the housing.

The dose setting member may be axially secured to the housing and may be freely rotatably supported relative to the housing. It may be due to the above mentioned axial displacement of the dose indicating member, that the axially fixed dose setting member is selectively and rotatably coupled with the dose indicating member, e.g. by means of correspondingly-shaped crown wheels provided on an upside facing side face of the dose indicating member and on a downward, hence inward facing portion of the ring-shaped dose setting member. The circumferential sidewall portion of the dose setting member is somewhat smaller in diameter compared to the correspondingly-shaped circumferential housing section. In this way, the dose setting member may be rotatably supported in the housing in a rather frictionless and smooth way.

In a further embodiment, a last dose limiting member is radially sandwiched between the sidewall portion of the dose setting member and the housing. The last dose limiting member may be threadedly engaged either with an outer thread of the sidewall portion of the dose setting member or with a correspondingly threaded inner portion of the housing. When threadedly engaged with the dose setting member, the last dose limiting member is typically rotatably locked to the housing. The last dose limiting member may be axially splined to the housing, i.e. it may be rotatably locked to the housing but may travel in axial direction relative to the housing depending on the lead and the rotational movement of the dose setting member. Typically, the last dose setting member comprises a radially outwardly extending protrusion guided in an axially extending and correspondingly-shaped notch or groove of the housing.

Additionally, there is provided a maximum or last dose stop, typically at the end of the threaded portion of the sidewall of the dose setting member. The dose setting member is exclusively rotatable during dose setting but may be locked to the housing when the drive mechanism is in dose injection mode. When rotating the dose setting member either in dose incrementing or dose decrementing direction, the last dose limiting member becomes subject to a respective axial displacement.

When a maximum number of doses, hence a maximum amount of medicament has been expelled or set by the drive mechanism, the last dose limiting member abuts with a radially outwardly extending stop, typically provided at the end of the threaded portion of the dose setting member. In this configuration, a further dose incrementing displacement of the dose setting member is effectively blocked.

In an alternative embodiment it is also conceivable, that the last dose limiting member is threadedly engaged with an inner thread of the housing while it features a radially inwardly extending protrusion or some other kind of positively interlocking feature to rotatably lock to the dose setting member.

Arranging the last dose limiting member between the dose setting member and the housing provides a rather direct force feedback to a user in the event that a last dose configuration or an end of content configuration has been reached. By means of the last dose limiting member, a dose incrementing rotation of the dose setting member relative to the housing can be effectively blocked by only one component directly engaging with the dose setting member and the housing, respectively. In this way, a rather direct and immediate feedback can be provided to the user, that the last dose or end of content configuration has been reached.

In another embodiment, the dose indicating member comprises a centrally located toothed through opening engaged with at least one resilient ratchet element in a dose setting configuration. The resilient ratchet element serves to block a self-actuated rotation of the dose indicating member under the action of the spiral spring element, e.g. at the end of a dose setting procedure. It is typically due to an axial displacement of the dose indicating member relative to the ratchet element, that the dose indicating member can be released therefrom, thereby allowing the dose indicating member to rotate in a dose decrementing direction under the action of the spiral spring element.

When displacing in axial direction during dose dispensing, the toothed through opening of the dose indicating member may axially disengage from the resilient ratchet element while another e.g. sound generating structure of the dose indicating member may audibly engage with the resilient ratchet element. In this way, a frequent and regular audible clicking sound can be generated during dose dispensing thereby indicating to a user, that dose dispensing is in progress.

The sound generating structure of the dose indicating member is axially offset but may be provided directly adjacent to the centrally located toothed through opening. For not blocking the dose decrementing rotation of the dose indicating member during dose dispensing, the sound generating structure may for instance comprise a saw toothed profile allowing the dose indicating member to rotate in dose decrementing direction.

In another aspect a drug delivery device for setting and dispensing of a dose of a medicament is provided for setting and dispensing of a dose of a medicament. The drug delivery device comprises a drive mechanism as described above and a cartridge at least partially filled with the medicament to be dispensed by the drug delivery. The cartridge is arranged in the housing of the drive mechanism or in a cartridge holder of the drug delivery device which is fixed to the housing either releasably or non-releasably, e.g. in case of a reusable or disposable drug delivery device, respectively. Consequently, the drug delivery device comprises a cartridge holder to receive and to accommodate a cartridge filled with the medicament.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, the dose setting member and/or the dose dispensing member are located at the proximal end of the drug delivery device. While the dose setting member provides a dose setting dial, directly operable by a user for setting of a dose the dose dispensing member, e.g. in form of a dose button is operable to be depressed in axial direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, a non-limiting embodiment of the invention will be described in detail, by making reference to the drawings, in which:

FIG. 5 shows a transverse cross-section through the drive mechanism, FIG. 6 shows the dose indicating member together with a locking member inside the housing in cross-section, FIG. 7 is illustrative of the last dose limiting member located on the outer circumference of the dose setting member.

DETAILED DESCRIPTION

Figures 1, 2:
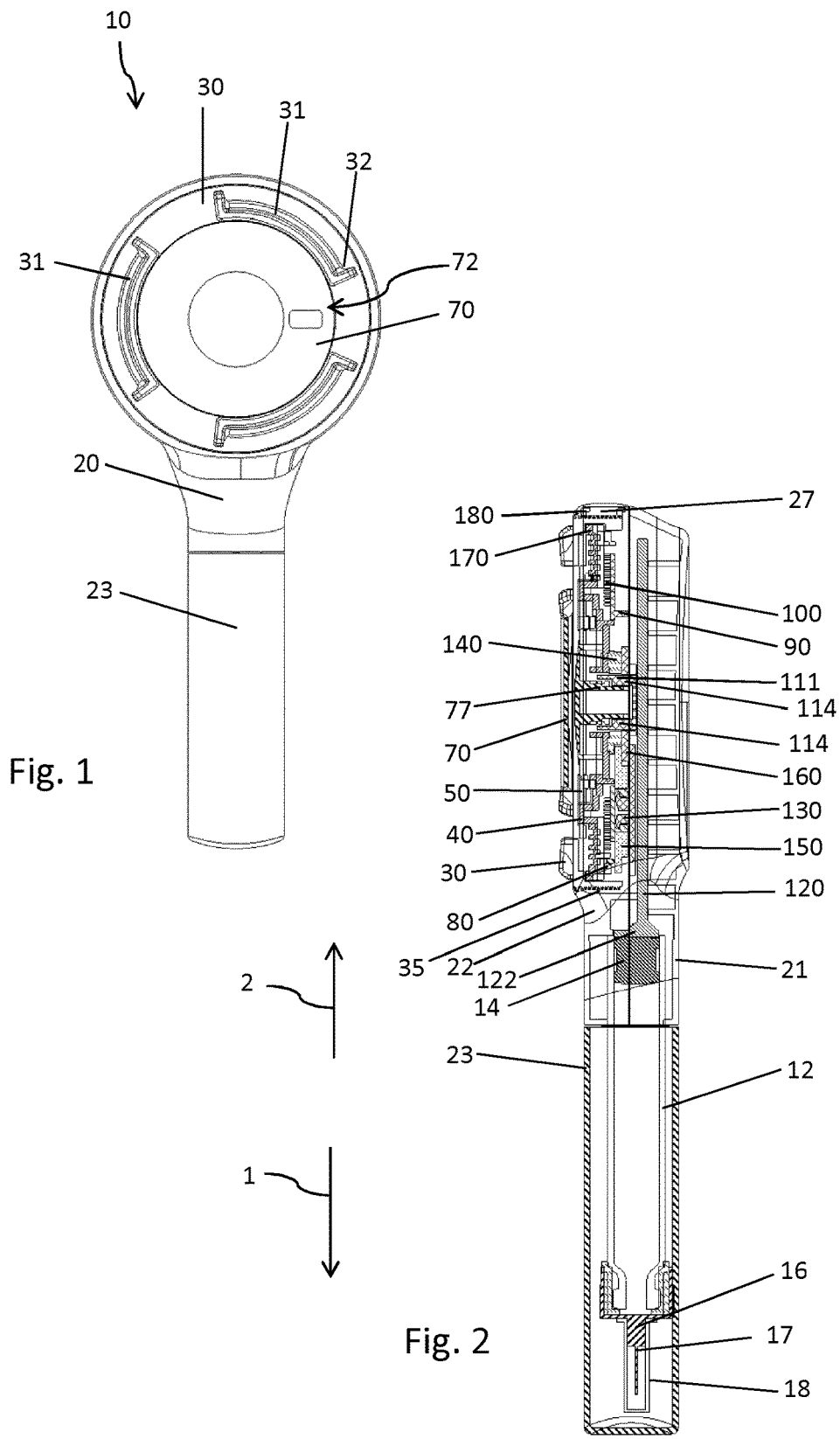
FIG. 1 shows the outer appearance of the drug delivery device.
FIG. 2 is a longitudinal cross-section through the drug delivery device.
Figure 8:
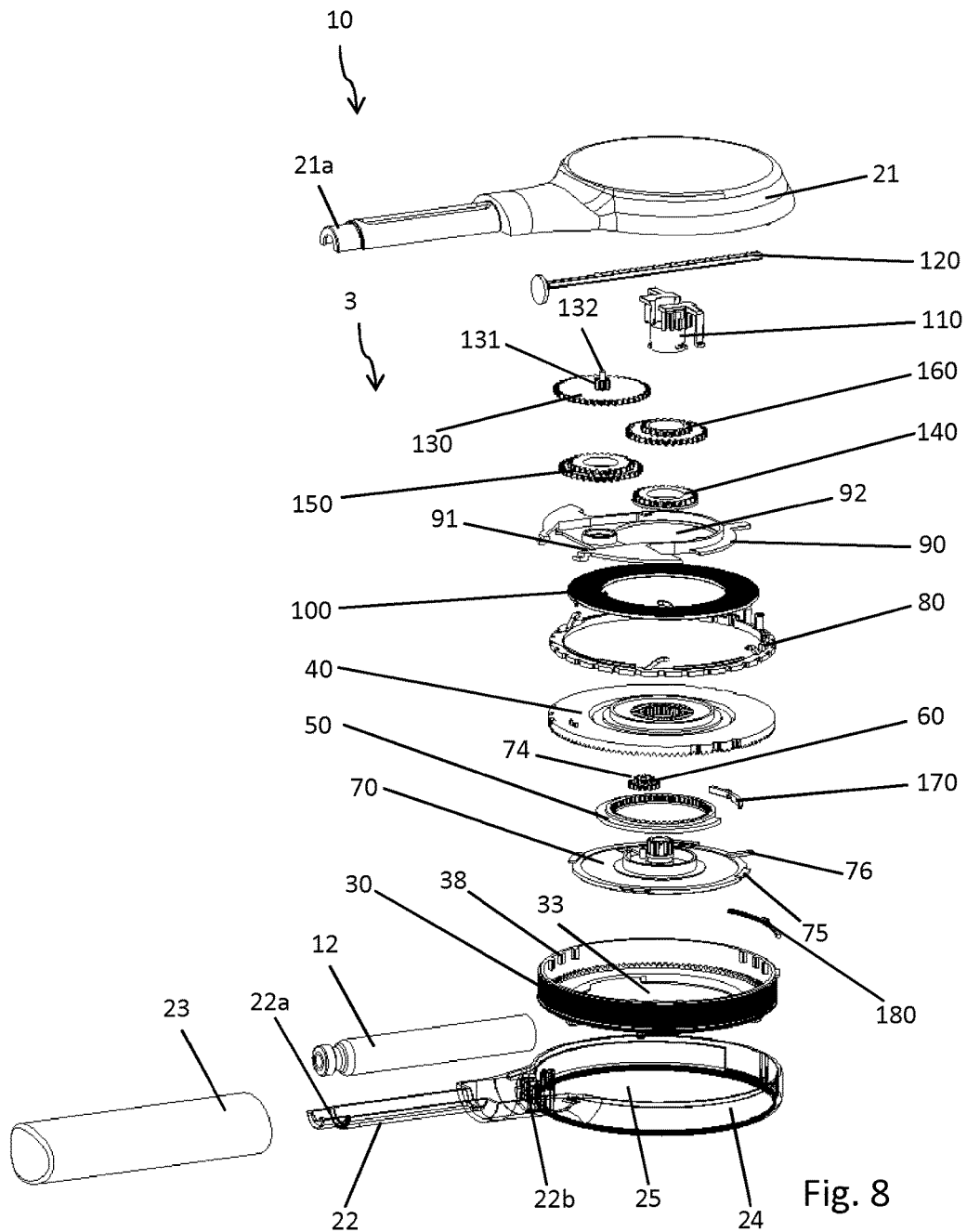
FIG. 8 is a perspective exploded view of the drug delivery device.
Figure 32:
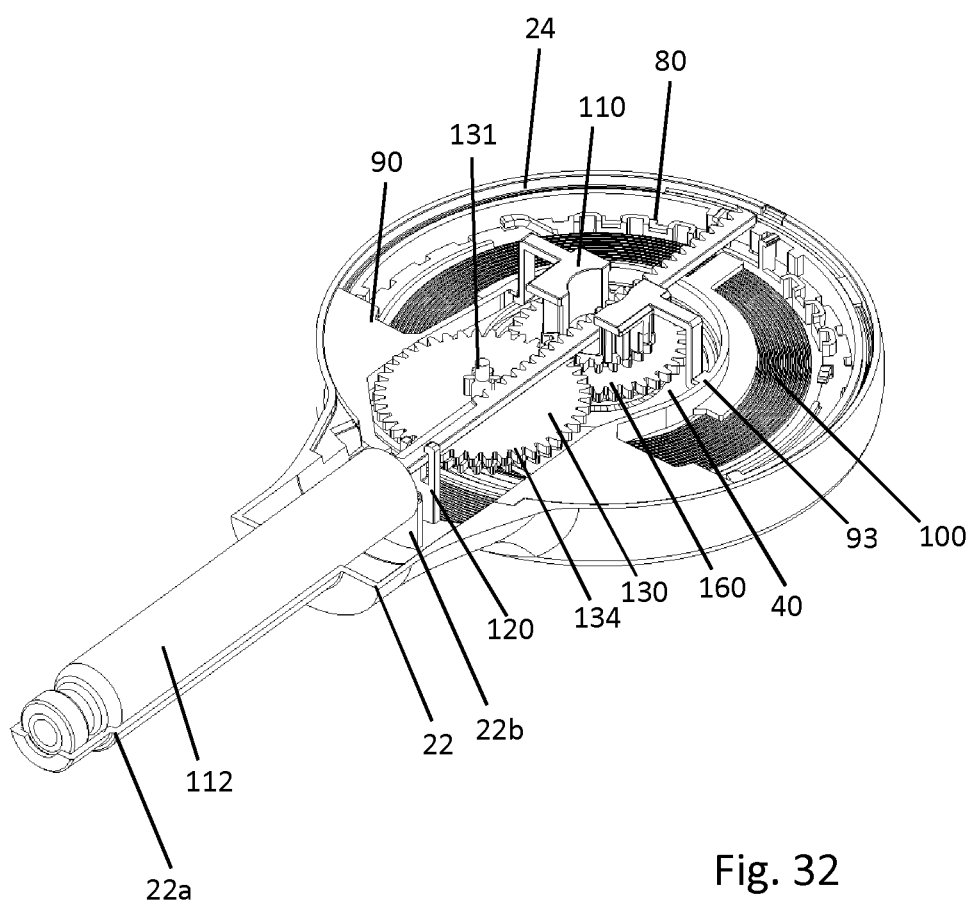
FIG. 32 shows the drug delivery device as seen from the bottom in a final stage of assembly without a lower housing component.

As illustrated in particular in FIGS. 1, 8 and 32 the drug delivery device 10 comprises at least in sections an elongated, substantially cylindrically-shaped housing 20. In distal direction 1, which faces towards the area of treatment during an injection procedure, the housing 20 comprises a cartridge holder section 21a, 22a as shown in FIG. 8 which is adapted to receive a cartridge 12, typically featuring a vitreous barrel and being filled with a medicament to be dispensed.

The cartridge 12 as illustrated in cross-section in FIG. 2 comprises a piston 14, by way of which the inner volume of the cartridge 12 is sealed in distal direction 2. The distal end of the cartridge 12 is typically provided with a pierceable seal, such like a septum, which is typically fastened and fixed to a neck portion of the cartridge 12 by way of a crimped cap. As shown in FIG. 2, a needle assembly 16 featuring a double tipped needle 17 is releasably attachable to the cartridge holder portion 21a, 22a of the housing 20. The needle assembly 16 typically comprises a threaded needle hub to be screwed on a correspondingly-shaped screwed socket provided on the distal end of the cartridge holder section 21a, 22a.

The needle assembly 16 is further provided with a removable needle cap 18. Moreover, the cartridge holder section 21a, 22a as shown in FIG. 8 is to be covered by a cylindrically-shaped and releasable protective cap 23.

The housing as shown in FIG. 8 comprises a lower housing component 21, which is illustrated to the top in FIG. 8 and an upper housing portion 22. Lower and upper housing components 21, 22 are adapted to either positively or frictionally engage upon final assembly of the drug delivery device 10. The cartridge holder portion 21a is integrally formed with the lower housing component 21 and the cartridge holder portion 22a is correspondingly integrally formed with the upper housing component 22.

Alternatively, it is also conceivable, that the cartridge holder portion is provided as a separate cylindrical sleeve releasably attachable to the housing 20. The drug delivery device 10 may be designed as a reusable device allowing to replace an empty cartridge 12 by a new one. Alternatively, the device 10 is provided and designed as a disposable device, which is intended to be discarded in its entirety once the content of the medicament provided in the cartridge 12 has been dispensed.

Figure 9:
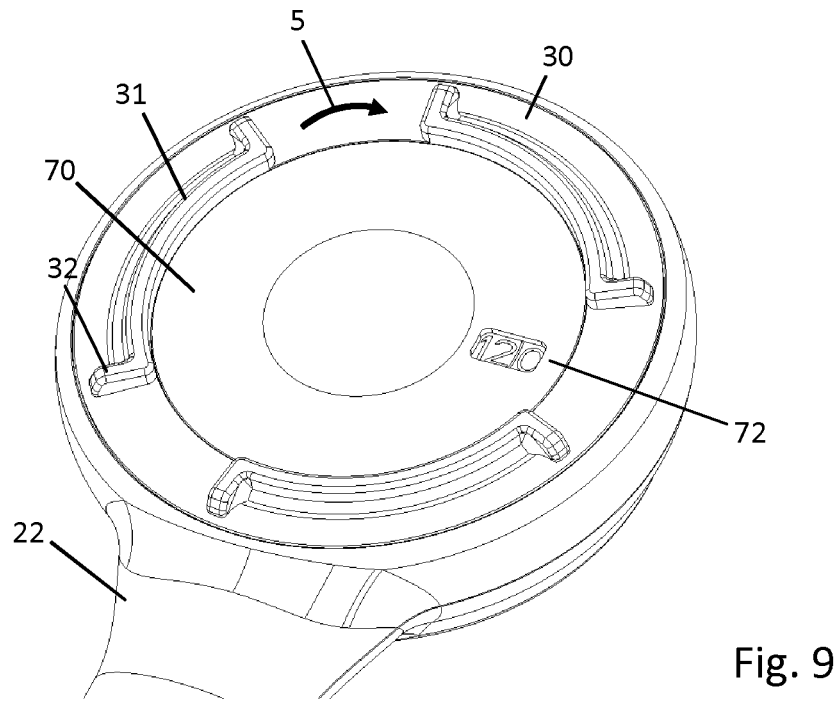
FIG. 9 shows a maximum dose configuration at the end of a dose setting procedure, FIG. 10 corresponds to the illustration according to FIG. 9 without dose setting member and without dose dispensing member.
Figure 10:
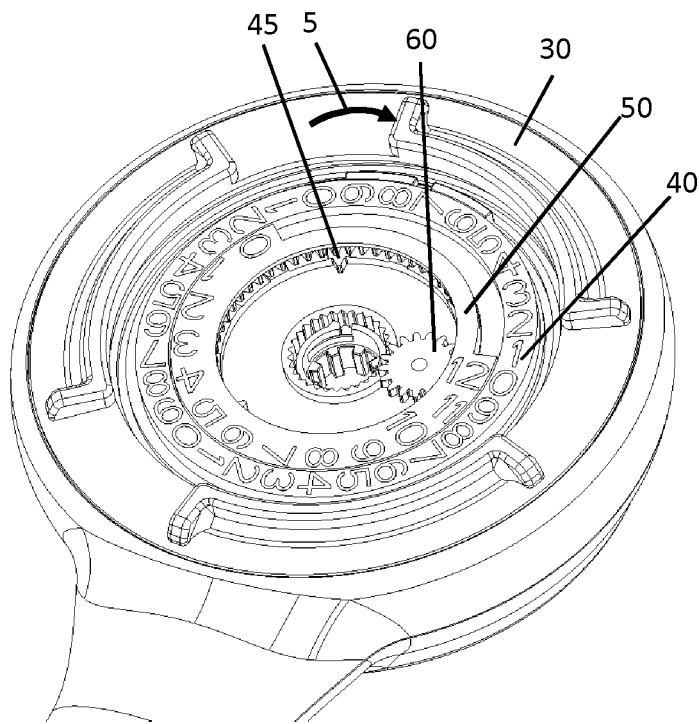

The proximal end of the housing 20 comprises a somewhat disc-like and hence circular shape. In particular, the upper housing component 22 comprises an annular or cylindrical-like sidewall 24 featuring a through opening 25 towards the top. As indicated in FIGS. 1, 9 and 10 the upward facing portion of the upper housing component 22 accommodates a ring-shaped dose setting member 30 and a dose dispensing member 70 located therein.

Figure 23:
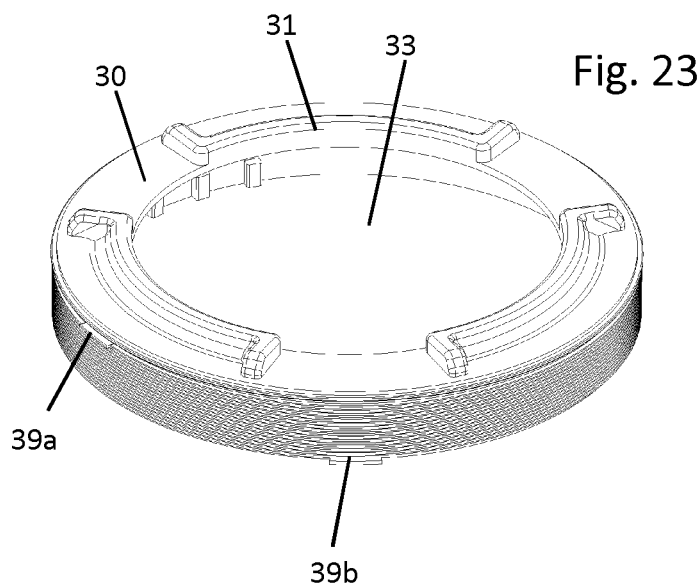
FIG. 23 shows an isolated perspective view of the dose setting member.
Figure 23A:
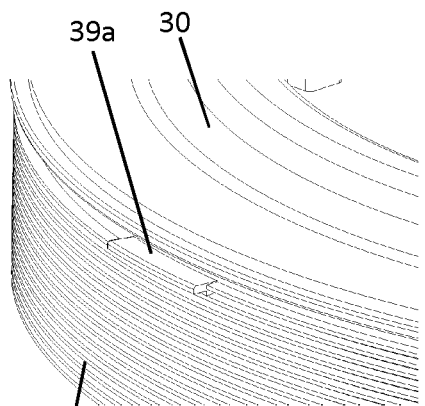
FIG. 23a shows an enlarged view of a radial stop and FIG. 23b shows an enlarged view of another radial stop provided on the outer circumference of the dose setting member.
Figure 23B:
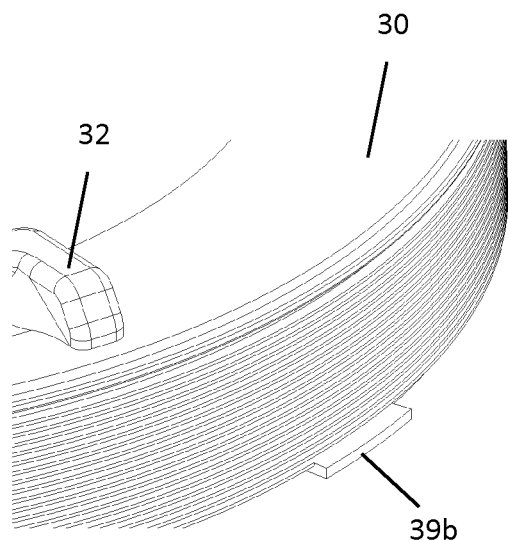

The dose setting member 30 as illustrated for instance in FIG. 23 comprises an annular-shaped sidewall 34 to be arranged in a radially overlapping configuration with the annular sidewall portion 24 of the upper housing component 22. Additionally, the dose setting member 30 comprises a radially inwardly extending flange, on which axially, hence upwardly extending gripping portions 31 are provided. The gripping portions 31 allow for an intuitive gripping and handling of the dose setting member 30 for rotating the same, e.g. in a clockwise, hence dose incrementing direction 5 as illustrated in FIG. 10.

The gripping portions 31 comprise a radially inwardly located arc shaped portion terminated by radially outwardly extending radial sections 32. In particular by the radial sections 32, a user may induce a dose setting torque to the dose setting member 30.

The dose setting member 30 comprises a central through opening 33 which is completely filled by the dose dispensing member 70 serving as a depressible dose button. The dose button 70 comprises a through opening 72 serving as a dose indicating window, through which dose size indicating digits of a dose indicating mechanism are visibly displayed.

The disc-shaped proximal end of the housing 20 allows for a comparatively flat and compact design. The radially outwardly extending bulged portions of the housing 20 further support an ergonomical handling of the drug delivery device 10 and may fit in a palm of a user's hand.

The drive mechanism 3 as shown in the various FIGS. 1-32 comprises a piston rod 120 featuring a widened pressure piece 122 at its distal end to engage with a proximal end face of the piston 14 of the cartridge 12. The piston rod 120 further comprises a toothed profile and may feature a respective rack portion 124 to engage with a pinion 131 of a drive wheel 130 rotatably supported in the housing 20 as illustrated for instance in FIG. 26.

Additionally, the drive mechanism 3 comprises a spring element 100 in form of a planar shaped spiral spring. Said spring element 100 is to be strained and biased during a dose setting procedure, thereby storing mechanical energy in the drive mechanism 3. Upon activating a dose dispensing procedure, the spring 100 will release its mechanical energy and will be coupled with the drive wheel 130 in such a way that the piston rod 120 is displaced in distal direction 1.

The drive mechanism 3 is almost completely located in the disc-shaped proximal section of the housing 20. Here, reference to axial direction 4 refers to the geometry of the disc-like shape of the proximal portion of the housing 20. The axial direction 4 is therefore specified by the axis of rotation of e.g. the dose setting member 30 or the dose indicating member 40.

In the following, setting of a dose is described.

Figure 24:
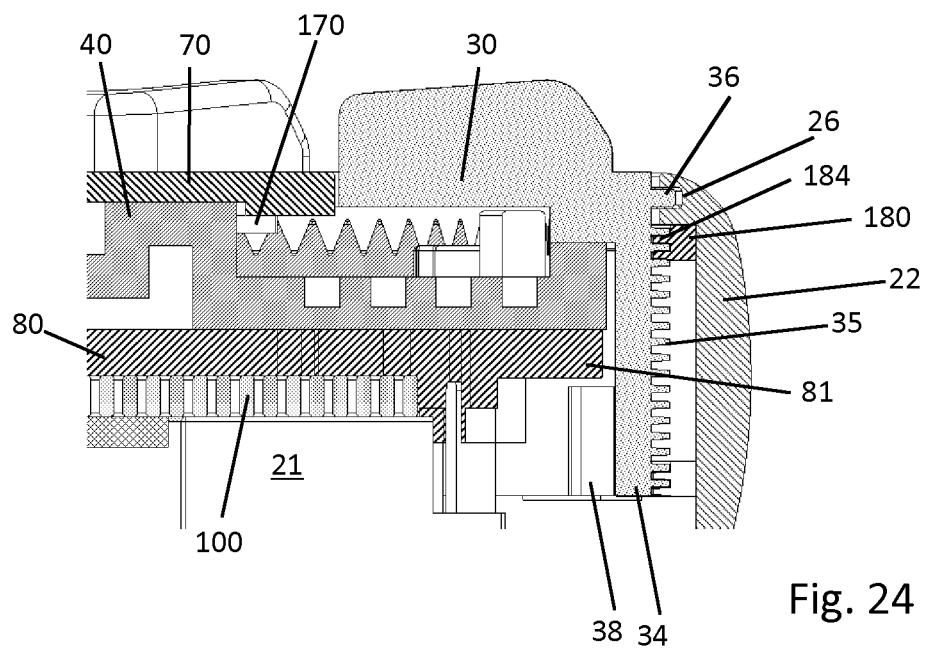
FIG. 24 shows a portion of the drive mechanism in cross-section during dose setting.

For setting of a dose, a user may take the drug delivery device 10 and may hold the lower housing component 21 in one hand while dialing the dose setting member 30 in a dose incrementing direction 5 with e.g. thumb and index finger of the other hand. As illustrated in FIG. 24, the dose setting member 30 comprises a radially outwardly extending rim 36 engaging with a correspondingly shaped groove 26 of the upper housing component 22. In this way, the dose setting member 30 is axially fixed relative to the housing 20.

Figure 4:
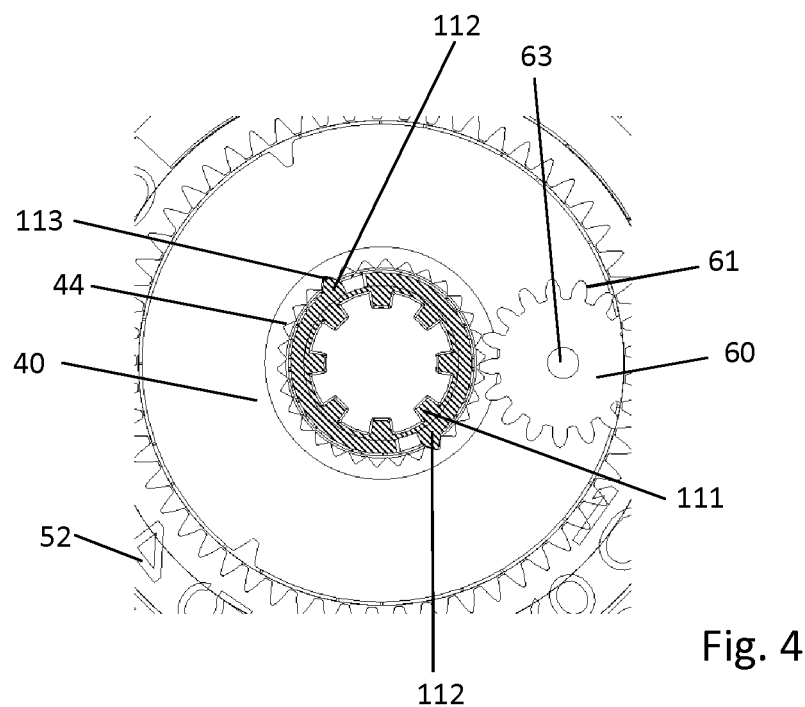
FIG. 4 is an enlarged view of the central portion of the dose indicating member according to FIG. 3.
Figure 16:
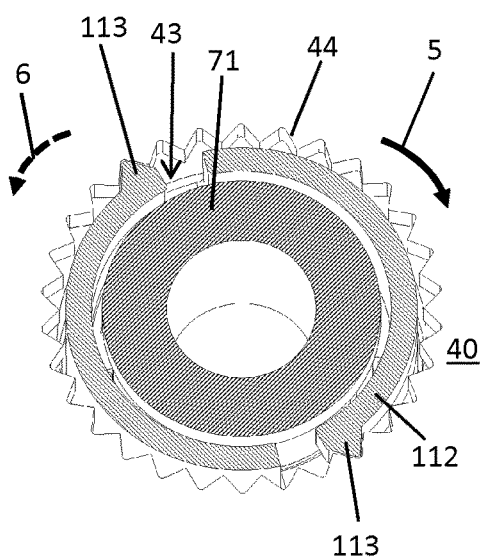
FIG. 16 shows a ratchet mechanism on the basis of a support member.
Figure 17:
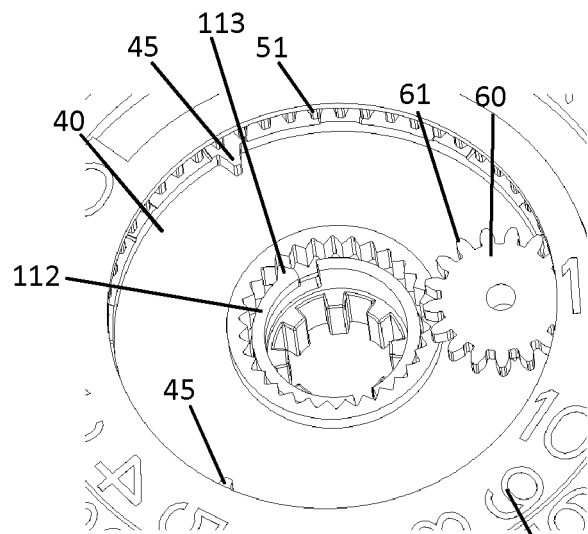
FIG. 17 shows the interaction of the dose indicating member with the ratchet mechanism in a perspective view.

Near its radially outwardly located sidewall portion 34, the dose setting member 30 comprises a crown wheel portion 37 to engage with a correspondingly shaped crown wheel portion 41 of the dose indicating member 40 located underneath. The dose indicating member 40 comprises a disc featuring a central through opening 43 with a toothed structure 44. As shown in FIGS. 4 and 16, the dose indicating member 40 is rotatably supported on an axially extending shaft portion 111 of a support member 110 separately illustrated in FIG. 15.

The support member 110 is fixedly attached to the housing 20 of the drive mechanism 3 by way of its radially outwardly extending fixing arms 118 provided with radially outwardly extending latch elements 119. Said latch elements 119 engage with radially inwardly extending fixing elements 93 of a frame 90 as shown in FIG. 32. The frame 90 is fixedly attached to the housing 20. It may be sandwiched or squeezed between upper and lower housing components 22, 21.

At an upper end, the shaft portion 111 of the support member 110 comprises two radially resiliently deformable ratchet elements 112. Said ratchet elements 112 are arc-shaped and feature a radially outwardly extending tooth 113 to mate with the toothed structure 44 of the dose indicating member's 40 through opening 43. Apart from producing a click sound upon rotating in dose incrementing direction 5 or dose decrementing direction 6 the radially outwardly biased ratchet elements 112 serve to rotatably lock the dose indicating member 40 and to secure the dose indicating member 40 against self-actuated spring driven rotation.

Figure 3:
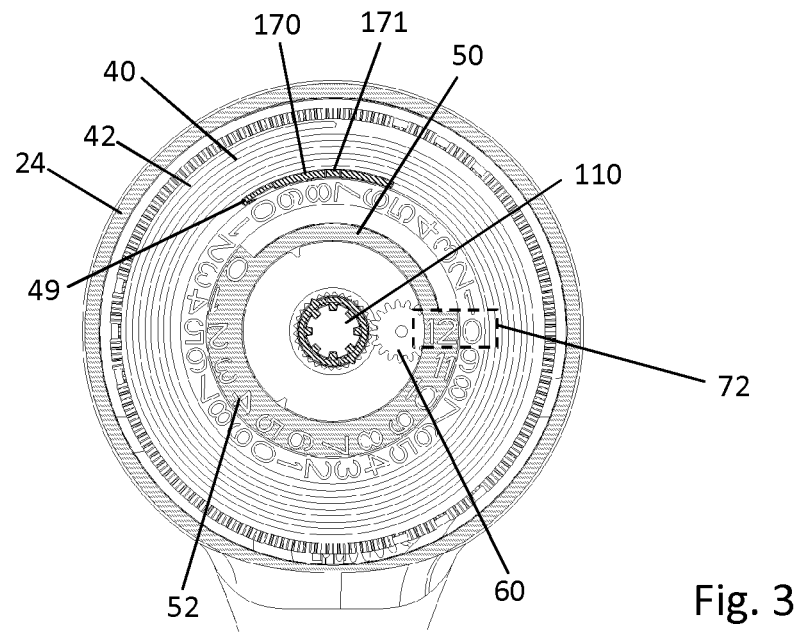
FIG. 3 illustrates a top view of the drive mechanism without dose setting and dose dispensing member.

The dose indicating member 40 comprises a disc-like shape and features a series of dose indicating digits 48 on its upward facing side face as indicated in FIGS. 3 and 10. The dose dispensing member 70 acting as a downwardly depressible dose button is rotatably fixed to the housing 20 via the support member 110. As for instance illustrated in FIGS. 15 and 27, the dose dispensing member 70 comprises an axially extending centrally located shaft 71 featuring radially outwardly extending protrusions 77 to engage with correspondingly-shaped grooves 115 located on a hollow inside facing sidewall portion of the shaft portion 111 of the support member 110. In this way, the dose dispensing member 70 can be displaced in axial direction 4 but remains rotatably locked and fixed to the support member 110 and hence to the housing 20.

Correspondingly, the shaft portion 110 comprises radially inwardly extending and axially extending protrusions 114 to mate with correspondingly-shaped recesses (not illustrated) of the shaft 71 of the dose dispensing member 70.

A rotation of the dose setting member 30 therefore equally transfers to the dose indicating member 40 located underneath, thereby indicating consecutive numbers 48 in the dose indicating window 72 in an incrementing manner during a dose incrementing rotation 5 and in a decrementing manner when dialed in the opposite, dose decrementing direction 6.

The dose dispensing member 70 comprises a downward pointing axially extending shaft 73 serving as a bearing for a gear wheel 60 as illustrated in FIG. 5. The gear wheel 60 comprises a toothed rim 61 meshing with a corresponding geared rim located on a radial inside facing geared portion 51 of a dose indicating ring 50. As indicated in FIG. 3, said dose indicating ring 50 provides a dose indicating information 52 in form another scale of digits, e.g. 0-12, representing tens or steps of ten, e.g. 10, 20, 30, 40, . . . , 120 in the dose indicating window 72. As illustrated in FIG. 3, the dose indicating member 40 comprises three consecutive scales from 0-9.

Accordingly, the dose indicating member 40 comprises three radially inwardly extending tapered portions 45 to mate with a respective tappet 62 of the gear wheel 60 located axially offset from the toothed rim 61 of the gear wheel 60. The tapered portions 45 are equidistantly arranged along the circumference of the dose indicating member 40. The mutual engagement between the tappet portion 45 and the tappet 62 is only active when the digit "9" of the dose indicating disc is followed by a "0" in the dose indicating window 72. Then, the rotation of the dose indicating member 40 is transferred to a respective rotation of the gear wheel 60, thereby rotating the dose indicating ring 50 one digit further.

By means of the mutually engaged dose indicating member 40 and the dose indicating ring 50, a rather large scale of variable dose sizes can be displayed in the dose indicating window 72 in steps of single units.

Figure 11:
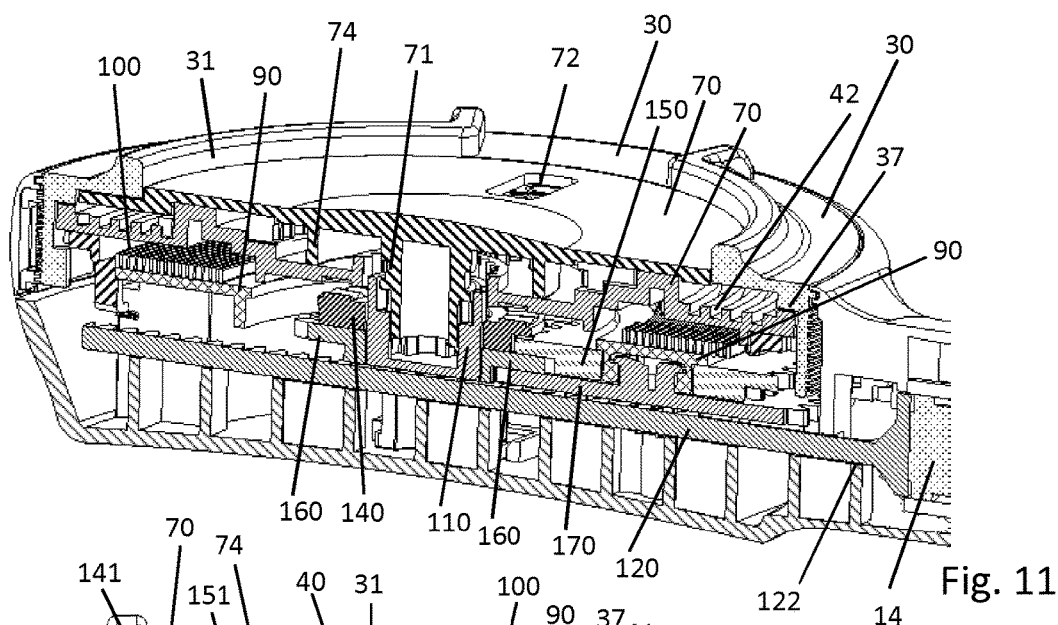
FIG. 11 shows another longitudinal cross-section through the drive mechanism.
Figure 12:
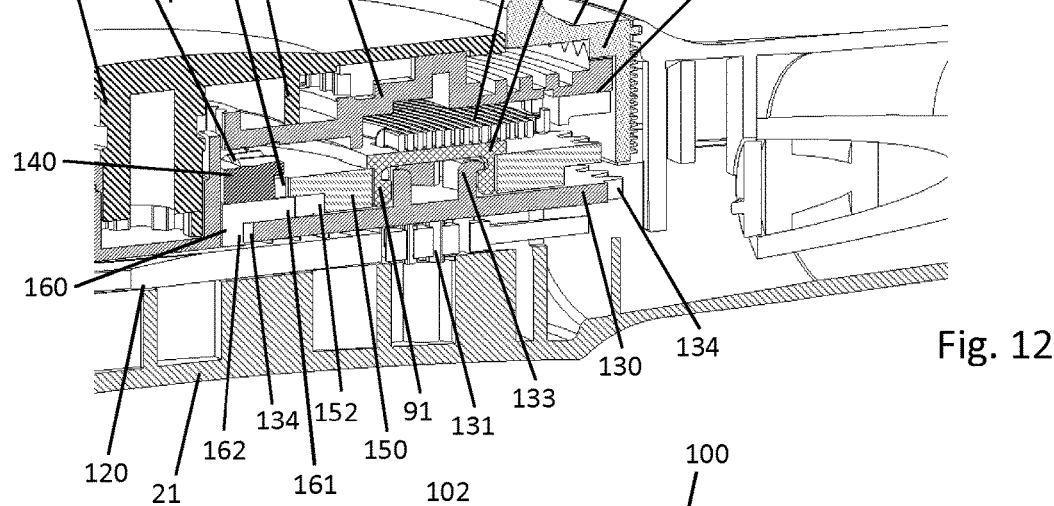
FIG. 12 shows a cross-section according to FIG. 11 from another perspective.
Figure 13:
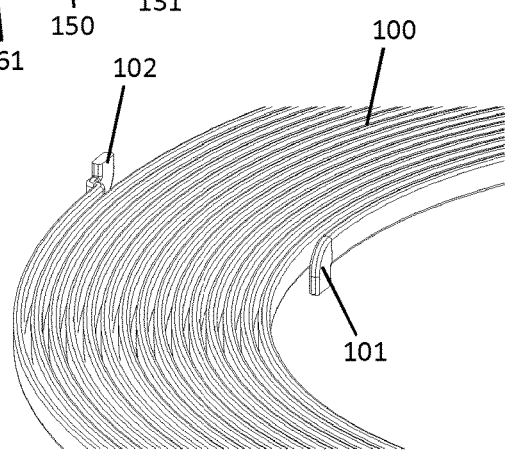
FIG. 13 shows a partial but isolated view of the spiral spring.
Figure 14:
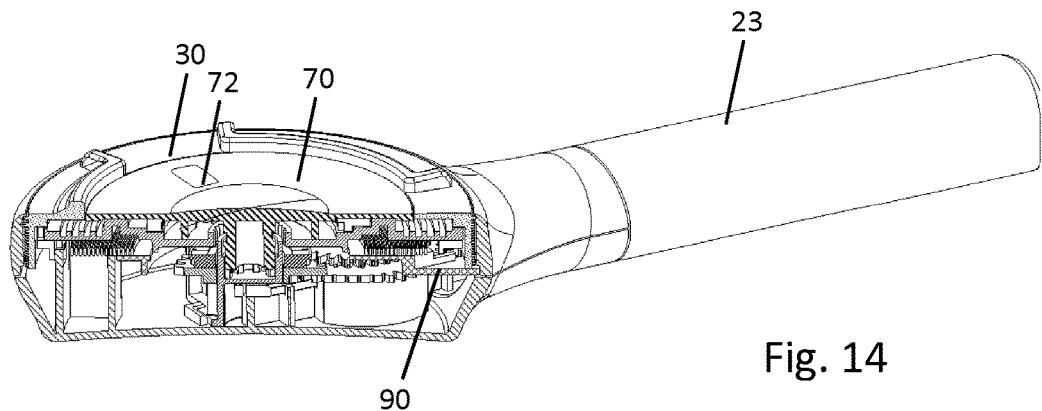
FIG. 14 shows another longitudinal cross-section through the drive mechanism.
Figure 15:
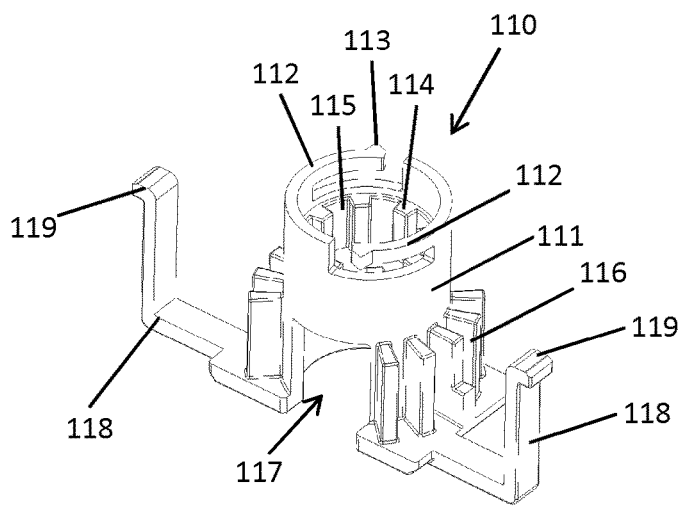

The dose indicating member 40 is furthermore directly interconnected with the spiral spring 100 as illustrated in detail in FIGS. 11-13. The spiral spring 100 comprises an upward pointing end section 102 at its radial outer circumference which is engaged with a correspondingly-shaped fastening structure provided on the lower face of the dose indicating member 40. A radially inwardly located opposite end section 101 points downwardly and is connected with the frame 90.

Since the frame 90 is fixedly attached in the housing 20 and since the dose indicating member 40 is permanently engaged with the spiral spring 100, a dose incrementing rotation 5 of the dose setting member 30 leads to a respective straining of the spiral spring 100. The dose indicating member 40 is hindered from rotating in a dose decrementing direction 6 by the engagement with the ratchet mechanism provided by the two diametrically oppositely located ratchet elements 112 of the support member 110. In this way, mechanical energy transferred to the spiral spring 100 during setting of a dose can be stored in the drive mechanism 3.

Figure 18:
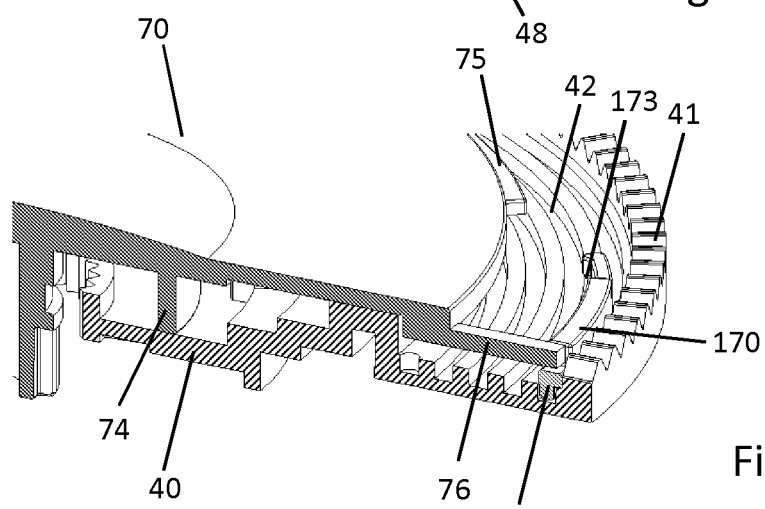
FIG. 18 shows the mutual interaction of the single dose limiting member, the dose dispensing member and the dose indicating member.
Figure 19:
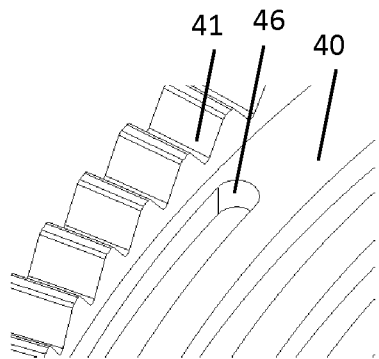
FIG. 19 is illustrative of a zero-dose stop.
Figure 20:
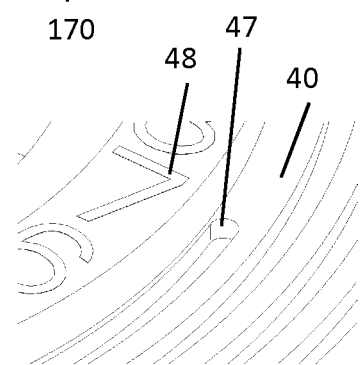
FIG. 20 shows a maximum dose stop provided on the dose indicating member.
Figure 30:
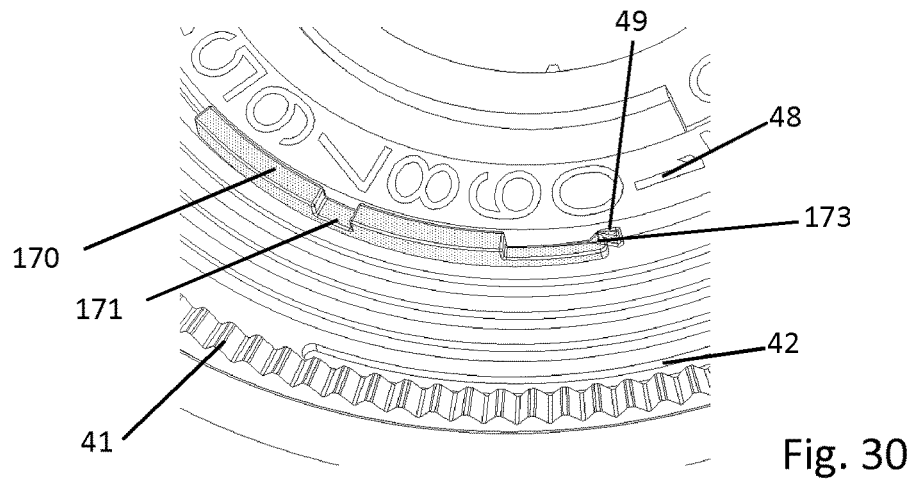
FIG. 30 is illustrative of the single dose limiting member in a zero-dose configuration.
Figure 31:
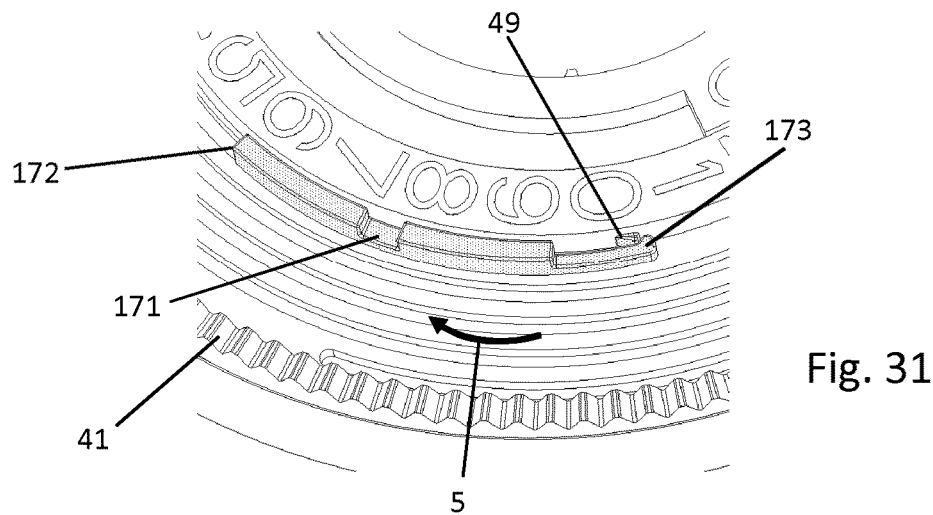
FIG. 31 shows the single dose limiting member prior to audibly reach a zero-dose configuration.

The drive mechanism is further provided with a single dose limiting mechanism implemented by means of a single dose limiting member 170 as shown in detail in FIGS. 18, 30 and 31. The upward facing portion of the dose indicating member 40 comprises a spiral-shaped groove 42 radially extending between the dose size indicating information 48 and the radially outwardly located crown wheel portion 41. In an initial zero-dose configuration, the single dose limiting member 170 is in circumferential and/or radial abutment with a radially extending stop 46 or stop face at the end of the spiral groove 42.

Additionally and as indicated in FIG. 18, the dose dispensing member 70 comprises a radially outwardly extending appendix 76 positively engaging with a notch 171 on the upward facing portion of the single dose limiting member 170. Since the dose dispensing member 70 is rotatably fixed to the housing 20, the single dose limiting member 170 is equally rotatably fixed relative to the housing 20.

When the dose indicating member 40 is subject to rotation, the single dose limiting member 170 is guided in the spiral groove 42 and may therefore experience a radially directed displacement relative to the housing 20, hence relative to the dose dispensing member 70. Radially adjacent to the dose indicating digits 48, the spiral groove 42 ends and provides a radial stop 47. When the single dose limiting member 170 engages with said stop 47, it serves to block a further dose incrementing rotation of the dose indicating member 40. This configuration typically corresponds to a maximum dose size of e.g. 120 IU of insulin, as for instance indicated in FIGS. 10, 30 and 31.

During a dose dispensing, which will be explained later on, the dose indicating member 40 is subject to a counter-directed dose decrementing rotation 6. Accordingly, the single dose limiting member 170 will travel along the spiral groove 42 in the opposite direction and will be displaced radially outwardly until a leading stop face 172 of the single dose limiting member 170 radially and/or circumferentially abuts with a respective radial stop 46 at the opposite end of the spiral groove 42.

Typically and as illustrated in FIGS. 30, 31 the single dose limiting member 170 comprises a radially resiliently deformable clicking member 173, e.g. located near at least one of its circumferential stop faces 172 or elsewhere in the single dose limiting member 170. The clicking element 173 is adapted to audibly engage with a correspondingly-shaped radially extending clicking member 49 provided near the zero-dose stop 46 and/or near the maximum dose stop 47 of the spiral groove 42. In this way, an audible click sound can be generated prior to the single dose limiting member 170 reaching its zero-dose configuration or its maximum dose configuration, e.g. at the end of a dose dispensing or dose setting procedure.

In this way, an audible feedback can be generated indicating to the user or patient, that a dose dispensing or dose setting procedure is just terminating.

Figure 25:
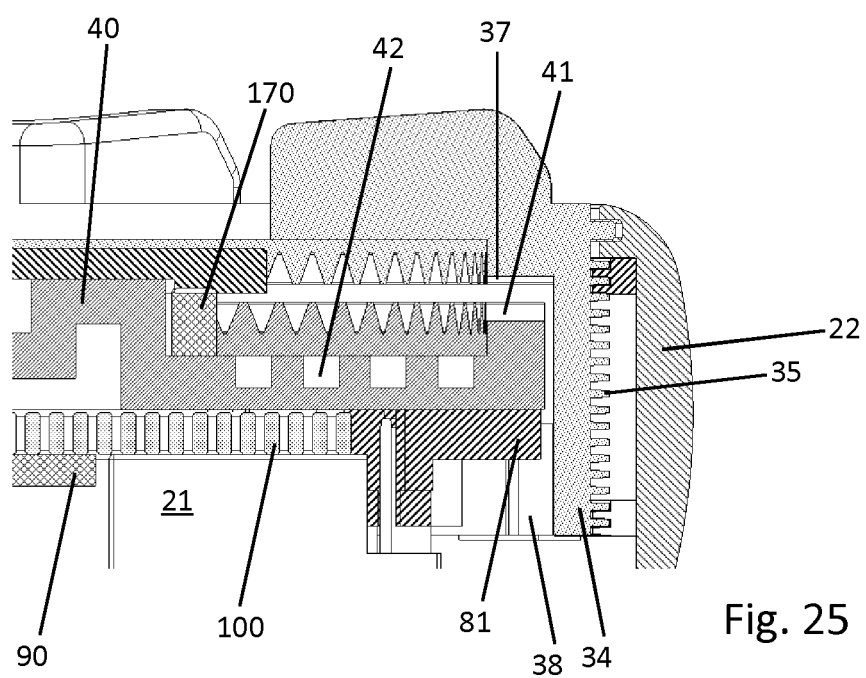
FIG. 25 shows the cross-section according to FIG. 24 during dose dispensing.

Additionally and as illustrated in more detail in FIGS. 23-25 there is also provided a last dose limiting member 180 featuring an arc-shaped geometry and being disposed radially between the sidewall portion 24 of the upper housing component 22 at the outer threaded portion 35 of the annular sidewall 34 of the dose setting member 30. The last dose limiting member 180 comprises an inner thread 184 to mate with the outer thread 35 of the dose setting member 30. Moreover and as illustrated in FIGS. 7, 21 and 22, the last dose limiting member 180 comprises a radially outwardly extending protrusion 183 to be axially guided in a correspondingly-shaped radially outwardly extending recess or groove 27 of the inside facing sidewall portion 24 of the upper housing component 22.

In this way, the last dose limiting member 180 is axially splined to the housing 20. The last dose limiting member 180 is only allowed to move in axial direction 4 relative to the housing. It is hindered from rotating with the dose setting member 30 during dose incrementing or dose decrementing. As a consequence, the last dose limiting member as illustrated in an initial configuration in FIGS. 24 and 25 will start to travel in an axial downward direction when the dose setting member 30 is rotated in a dose incrementing direction 5. Accordingly, when the dose setting member 30 is rotated in a dose decrementing direction, the last dose limiting member 180 is subject to an upwardly directed axial displacement, e.g. during dose correction.

Figure 21:
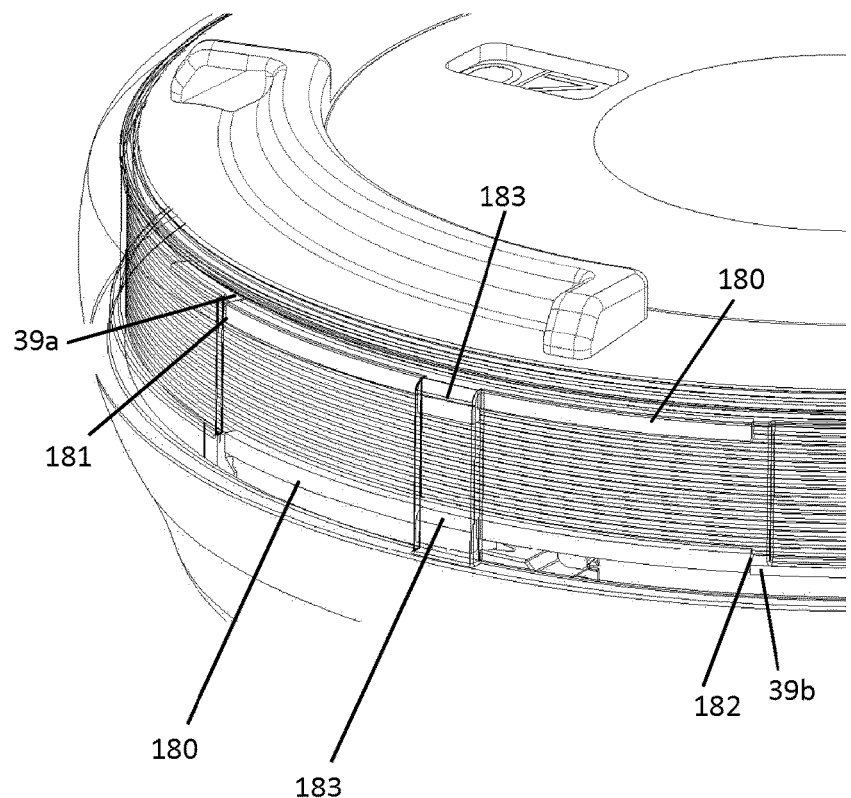
FIG. 21 is illustrative of the last dose limiting member radially sandwiched between the housing and the dose setting member.
Figure 22:
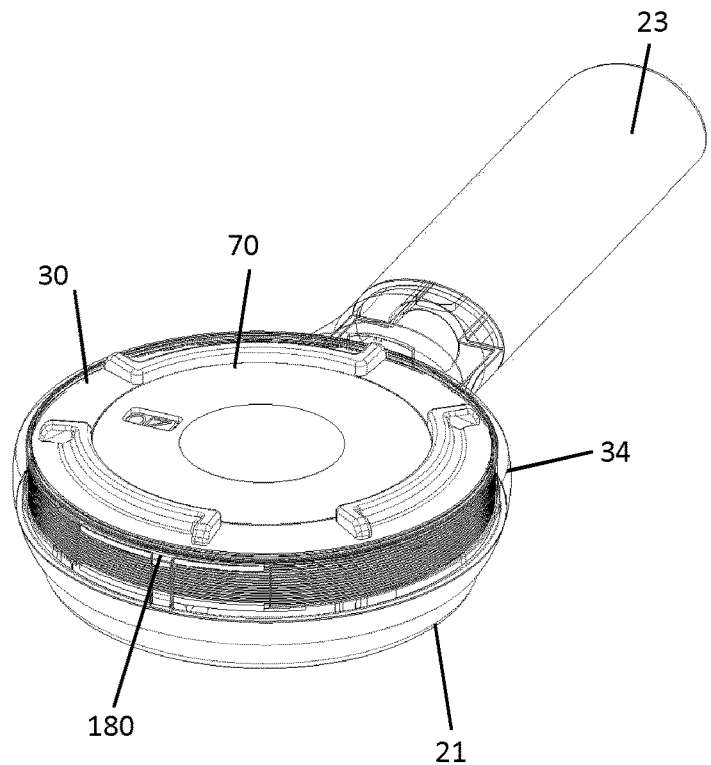
FIG. 22 shows another view of the dose limiting member according to FIG. 21.

In FIGS. 7, 21 and 22, the last dose limiting member 180 is illustrated in both of its end configurations. At an upper end of the outer threaded portion 35 of the dose setting member 30 there is provided a radially outwardly extending radial stop 39*a* whereas another correspondingly shaped radially outwardly extending stop 39*b* is provided at an axial opposite end portion of the outer thread 35. The radial stop 39a is adapted to abut with a respective stop face 181 of the last dose limiting member 180.

This stop configuration corresponds to a zero-dose configuration prior to a first setting and dispensing of a dose. As the drug delivery device 10 and the drive mechanism 3 is used repeatedly for individually setting and dispensing of a dose, the last dose limiting member 180 consecutively travels downwardly in axial direction until its opposite stop face 182 engages with the last dose stop 93b. When reaching this stop configuration, the dose setting member 30 is immediately blocked from being rotated further in dose incrementing direction 5. In this way it can be effectively prevented, that a dose exceeding the residual filling level or exceeding the amount of medicament left in the cartridge 12 can be set and subsequently dispensed in an inaccurate way.

Since the last dose limiting member 180 is sandwiched between and is engaged with both, the housing 20 and the dose setting member, an immediate and precise blocking feedback can be provided to a user when the last dose configuration has been reached.

In the following, dispensing of a dose is described.

For dispensing of a dose, the user simply depresses the dose dispensing member 70 in axial direction 4 as indicated in FIG. 5. Since the disc-shaped dose button or dose dispensing member 70 comprises an axially extending annular rim 74 in axial abutment with the dose indicating member 40, the downward directed axial displacement of the dose dispensing member 70 is equally transferred to the dose indicating member 40.

In this way, the crown wheel 41 of the dose indicating member 40 disengages from the correspondingly shaped crown wheel portion 37 of the dose setting member 30. As further illustrated in FIG. 5, there is provided a ring-shaped locking member 80 axially sandwiched between the frame 90 and the dose indicating member 40. Said locking member 80 further comprises at least one axially extending and axially resiliently deformable integrated dispensing spring element 84. In this way, the combined depression of the dose dispensing member 70 and the dose indicating member 40 occurs against the action of the dispensing spring element 84.

Moreover, the locking member 80 as illustrated in cross-section in FIG. 6 comprises an axially extending slot 82 to receive a correspondingly-shaped axially extending locking pin 28 of the housing 20. By means of the locking pin 28 the locking member 80 is rotatably fixed to the housing 20. Additionally, the locking member 80 comprises a radially toothed structure 81 along its outer circumference. The toothed structure 81 is disengaged from a radially inwardly extending and correspondingly-shaped toothed structure or protrusion 38 extending radially inwardly from the sidewall 34 of the dose setting member 30.

As illustrated in FIG. 24, when the toothed structure 81 and the protrusions 38 are not yet engaged, the dose setting member 30 can be freely rotated. However, depression of the dose dispensing member 70 and the dose indicating member 40 together with the locking member 80 axially displaces the toothed structure 81 in an overlapping and engaging configuration with the protrusions 38 of the dose setting member 30. In this way, the dose setting member 30 can be rotatably locked during dose dispensing.

Since the locking member 80 is rotatably fixed to the housing 20, the mutual engagement of locking member 80 and dose setting member 30 effectively blocks a further rotation of the dose setting member 30 while the drive mechanism 3 is in dose dispensing mode. In this way, it can be effectively prevented, that the dose setting member 30 and hence the last dose limiting member 180 is manipulated during dose dispensing.

Figure 29:
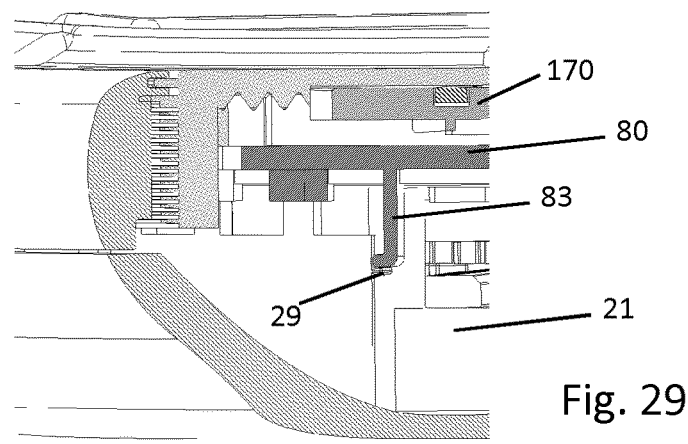
FIG. 29 shows another cross-section of the drive mechanism.

Additionally and as illustrated in FIG. 6 and FIG. 29, the locking member 80 comprises axially extending clicking elements 83 that reach into a slot of the lower housing component 21. In said slot there are provided radially inwardly extending protrusions 29 engaging with the radially resiliently deformable clicking elements 83 of the locking member 80. When pressing down the locking member 80 at the beginning of a dispensing procedure, the mutual engagement of the clicking elements 83 with the radial protrusions 29 serve to generate an audible feedback to the user that the dose dispensing procedure begins. Accordingly, when releasing the dose dispensing member, typically at the end of a dispensing procedure, the clicking elements repeatedly engage with the protrusions 29 thereby audibly indicating that the device is switched into dose setting mode.

The downwardly or inwardly directed axial displacement of the dose indicating member 40 equally transfers to the toothed structure 44 of its central though opening 43. As a consequence and as it is apparent from a comparison of FIGS. 27 and 28, the ratchet elements 112 release the toothed structure 44 thereby allowing that the dose indicating member 40 starts to rotate in a dose decrementing direction 6 under the action of the relaxing spiral spring element 100.

The torque exerted by the spring 100 to the dose indicating member 40 is transferred to a gear wheel 140 featuring a crown wheel portion 141 on its side face facing towards the lower face of the dose indicating member 40. In order to transfer a respective driving torque to the gear wheel 140, the dose indicating member 40 comprises a correspondingly-shaped crown wheel 41a at its lower surface. Typically, the teeth of the mutually engaging crown wheels 41a, 141 are such, that a torque transmission between the spring driven dose indicating member 40 and the gear wheel 140 is already established before the toothed structure 44 of the dose indicating member 40 disengages from the ratchet elements 112 of the support member 110. In this way a substantially slipless clutch for switching between the dose setting mode and the dose dispensing mode can be effectively provided.

The gear wheel 140 is rotatably supported by the shaft portion 111 of the support member 110. As becomes apparent from FIG. 26, the gear wheel 140 comprises an outer geared rim 142 engaged with a correspondingly-shaped upper toothed rim 151 of another gear wheel 150. As illustrated in FIG. 12, gear wheel 150 is rotatably supported by an axially extending shaft portion 91 of the frame 90. The gear wheel 150 further comprises a lower toothed rim 152 axially offset from the upper toothed rim 151.

The lower toothed rim 152 meshes and mates with an upper toothed rim 161 of another gear wheel 160. Said gear wheel 160 is rotatably supported by the shaft 111 of the support member 110. It is arranged coaxial to the gear wheel 140. As further illustrated in FIG. 12, the gear wheel 160 also comprises a lower toothed rim 162 that meshes with an outer toothed rim 134 of a drive wheel 130. As illustrated in FIG. 12, said drive wheel 130 is rotatably supported in the shaft portion 91 of the frame 90. For this purpose, the drive wheel 130 comprises axially extending and radially resiliently deformable shaft elements 133 to positively engage with a correspondingly-shaped recessed structure at the inside facing portion of the shaft portion 91.

Axially offset from its toothed rim 134, the drive wheel 130 comprises a pinion 131 or sprocket operably engaged with the rack portion 124 of the piston rod 120. The gearing set up by the various gear wheels 140, 150, 160 and the drive wheel 130 provides a required transmission gear in order to provide a required transmission ratio between the rotation of the dose indicating member 40 and a respective distally directed translational displacement of the piston rod 120.

Figure 26:
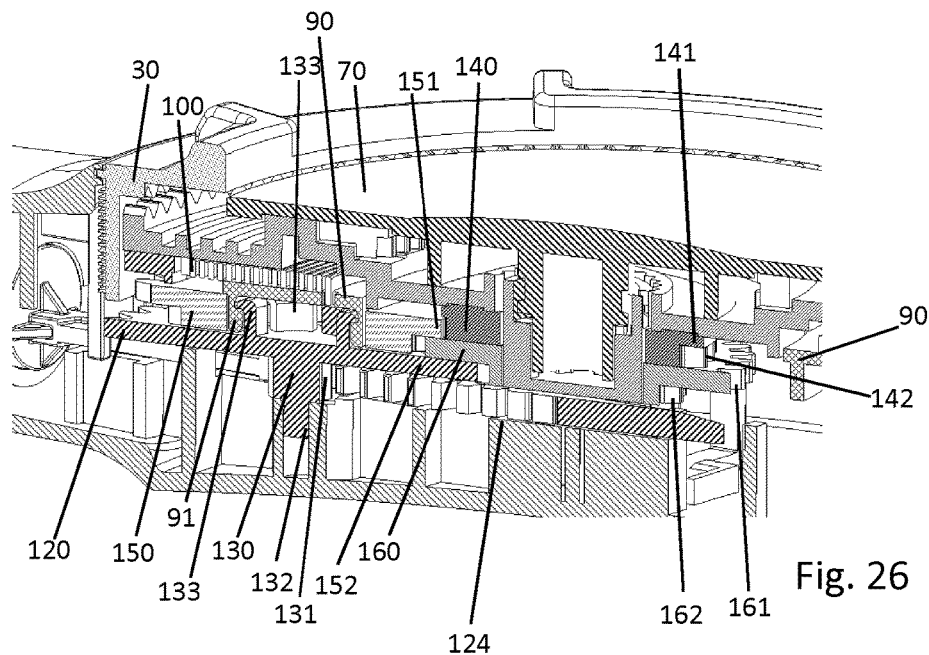
FIG. 26 is illustrative of another perspective cut view of the drive mechanism.
Figure 27:
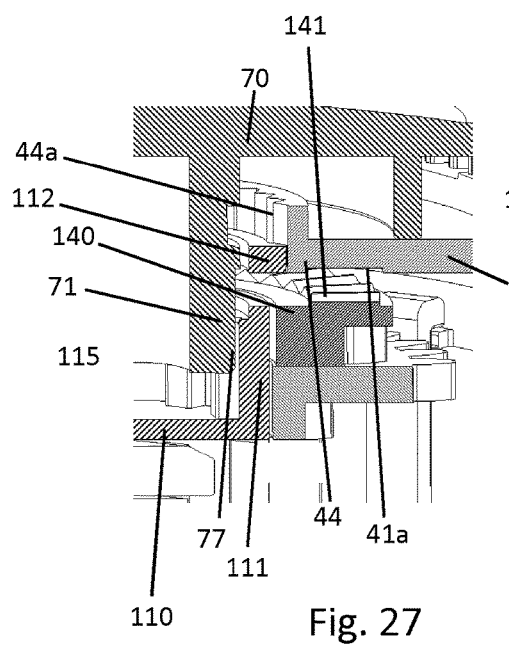
FIG. 27 shows the mutual interaction of the ratchet member with the dose indicating member during dose setting and FIG. 28 is indicative of the interaction between the ratchet element and the dose indicating member in dose dispensing mode.

As further illustrated in FIG. 26, the drive wheel 130 comprises a pin 132 axially extending from the pinion 131. Said pin 132 is located and supported by a correspondingly shaped receptacle or bearing of the lower housing component 21. In this way, the drive wheel 130 is radially constrained on both sides of the piston rod 120. In this way, mechanical play or backlash that may otherwise arise from a loose fitting of the drive wheel 130 can be reduced to a minimum.

If a user prematurely releases the dose dispensing member 70 before the end of a dispensing procedure has been reached, the locking member 80, the dose indicating member 40 and the dose dispensing member 70 will return into their initial position under the effect of the dispensing spring element 84. In the course of such an upwardly directed axial displacement, the interlocking engagement of the dose indicating member 40 and the ratchet elements 112 will be immediately re-established even before a torque transmitting mutual engagement between the gear wheel 140 and the dose indicating member 40 is abrogated.

Distally directed displacement of the dose dispensing member 70 under the action of the dispensing spring element 84 is delimited by means of at least one radially extending axial stop 75 provided at the outer circumference of the dose dispensing member 70. Said stop 75 will engage with a radially inwardly located rim of the dose setting member 30. In this way, the dose dispensing member 70 can be axially secured in the upward direction.

As illustrated in the cross-section according to FIG. 5, the piston rod 120 extends through a passageway 117 extending in distal direction through a base portion 116 of the support member 110. The support member 110 can be fastened to the bottom of the lower housing component 21 by means of axially upwardly extending latching elements 21b engaging with the base portion 116 of the support member 110.

Figure 28:
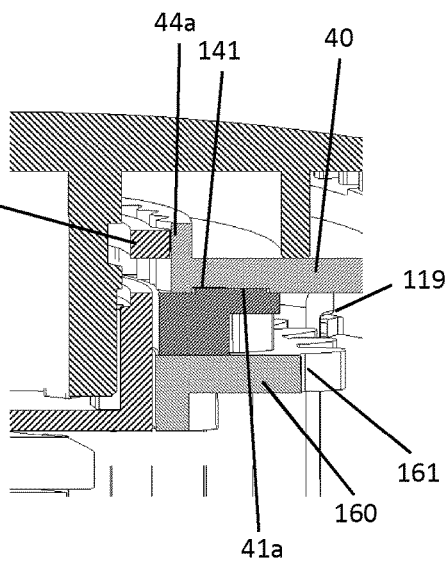

The through opening 43 of the dose indicating member 40 comprises a click sound generating structure 44a axially adjacent to the toothed structure 44. When in dispensing mode as illustrated in FIG. 28, the ratchet elements 112 may audibly engage with said click sound generating structure 44a, thereby audibly indicating to a user, that a dose dispensing procedure is in progress. This audible feedback can be provided in addition to the inherent visual feedback of the dose indicating window 72 during a dose dispensing procedure.

In FIG. 32 the final step of assembly of the drug delivery device 10 is illustrated. Here, all functional components of the drive mechanism except the lower housing component 21 are assembled to the frame 90 and/or to the upper housing component 22. Moreover also the cartridge 12 is appropriately arranged in the respective cartridge holder portion 22a. Since the device is initially in dose setting mode, the piston rod 120 can be displaced in distal direction 1 until its pressure piece 122 abuts with the piston 14 of the cartridge 12. During this final step of assembly, the drive wheel 30 may be set in a rotative movement. Since the gearing provided by the various gear wheels 130, 140, 150, 160 is operably disconnected from the dose indicating member 40 and the various dose limiting members 170, 180, this initial manipulation of the drive mechanism 3 is substantially effect less on the dose indicating mechanism.

Distally directed displacement of the piston rod 120 may also be induced by a manual rotation of the drive wheel 130. Naturally, the upper housing component 21 further comprises a guiding structure 22b to translationally guide the piston rod 120 in distal direction 1. Furthermore, the gear wheels 140, 160 are arranged inside and extend through a central through opening 92 of the frame 90. Hence, the drive mechanism 3 extends above and below the frame 90.

LIST OF REFERENCE NUMERALS

1 distal direction
2 proximal direction
3 drive mechanism
4 axial direction
5 dose incrementing direction
6 dose decrementing direction
10 drug delivery device
12 cartridge
14 piston
16 needle assembly
17 needle
18 needle cap
20 housing
21 lower housing component
21a cartridge holder portion
21b latching element
22 upper housing component
22a cartridge holder portion
22b guiding structure
23 protective cap
24 sidewall
25 through opening
26 groove
27 recess
28 pin
29 protrusion
30 dose setting member
31 gripping portion
32 radial section
33 through opening
34 sidewall
35 outer thread
36 rim
37 crown wheel
38 protrusion
39a radial stop
39b radial stop
40 dose indicating member
41 crown wheel
41a crown wheel
42 groove
43 through opening
44 toothed structure
44a sound generating structure
45 tappet portion
46 radial stop
47 radial stop
48 dose indicating information
49 clicking member
50 dose indicating ring
51 geared portion
52 dose indicating information
60 gear wheel
61 toothed rim 62 tappet
63 bearing
70 dose dispensing member
71 shaft
72 dose indicating window
73 shaft
74 rim
75 axial stop
76 appendix
77 protrusion
80 locking member
81 toothed structure
82 slot
83 clicking element
84 dispensing spring element
90 frame
91 shaft portion
92 through opening
93 fixing element
100 spring element
101 end section
102 end section
110 support member
111 shaft portion
112 ratchet element
113 tooth
114 protrusion
115 groove
116 base portion
117 passageway
118 fixing arm
119 latch element
120 piston rod
122 pressure piece
124 rack portion
130 drive wheel
131 pinion
132 pin
133 shaft element
134 toothed rim
140 gear wheel
141 crown wheel
142 geared rim
150 gear wheel
151 upper toothed rim
152 lower toothed rim
160 gear wheel
161 upper toothed rim
162 lower toothed rim
170 single dose limiting member
171 notch
172 stop face
173 clicking element
180 last dose limiting member
181 stop face
182 stop face
183 protrusion
184 inner thread

The invention claimed is:

1. A drive mechanism of a drug delivery device for setting and dispensing of a dose of a medicament, the drive mechanism comprising:
a housing;
a piston rod to operably engage with a piston of a cartridge for displacing the piston in a distal direction;
a dose indicating member with dose size indicating numbers or symbols thereon, wherein the dose indicating member is connected to a spring element and is rotatable in a dose incrementing direction against an action of the spring element for setting of the dose, and wherein the dose indicating member is rotatable in a dose decrementing direction under an action of the spring element for dispensing of the dose, the dose decrementing direction being opposite to the dose incrementing direction; and
a drive wheel operably engaged with the piston rod for displacing the piston rod in the distal direction for dose dispensing,
wherein the dose indicating member is engageable with the drive wheel during dose dispensing to transfer a driving force to the drive wheel when driven by the relaxing spring element in a dose decrementing direction.

2. The drive mechanism according to claim 1, wherein the dose indicating member comprises a flat-shaped dose indicating disc.

3. The drive mechanism according to claim 1, wherein the spring element comprises a spiral spring having a first end section connected to the housing and having a second end section connected to the dose indicating member.

4. The drive mechanism according to claim 1, further comprising a ring-shaped dose setting member rotatably supported by the housing and being selectively engageable with the dose indicating member for setting of the dose.

5. The drive mechanism according to claim 4, wherein the ring-shaped dose setting member comprises a circumferential side wall portion extending into the housing.

6. The drive mechanism according to claim 5, wherein a last dose limiting member radially sandwiched between the side wall portion and the housing is threadedly engaged with the side wall portion and rotatably locked to the housing.

7. The drive mechanism according to claim 1, further comprising a dose dispensing member rotatably fixed to the housing and being depressible in an axial direction against an action of a dispensing spring element.

8. The drive mechanism according to claim 7, wherein the dose indicating member axially abuts with the dose dispensing member.

9. The drive mechanism according to claim 7, wherein the dose dispensing member comprises a through opening serving as a dose indicating window through which a portion of the dose size indicating numbers of symbols of the dose indicating member is visibly displayed.

10. The drive mechanism according to claim 7, wherein a dose dispensing member is radially enclosed by a dose setting member.

11. The drive mechanism according to claim 1, wherein the dose indicating member comprises a spiraled groove to engage with a single dose limiting member.

12. The drive mechanism according to claim 11, wherein the single dose limiting member is radially displaceable relative to a dose dispensing member along the spiraled groove and is rotatably fixed to the dose dispensing member.

13. The drive mechanism according to claim 12, wherein the dose dispensing member comprises a radially outwardly extending appendix engaged with a notch of the single dose limiting member.

14. The drive mechanism according to claim 1, wherein the dose indicating member comprises a centrally located toothed through opening engaged with at least one resilient ratchet element in a dose setting configuration.

15. A drug delivery device for setting and dispensing of a dose of a medicament, the drug delivery device comprises:
- a drive mechanism comprising:
  - a housing;
  - a piston rod to operably engage with a piston of a cartridge for displacing the piston in a distal direction;
  - a dose indicating member with dose size indicating numbers or symbols thereon, wherein the dose indicating member is connected to a spring element and is rotatable in a dose incrementing direction against an action of the spring element for setting of the dose, and wherein the dose indicating member is rotatable in a dose decrementing direction under an action of the spring element for dispensing of the dose, the dose decrementing direction being opposite to the dose incrementing direction; and
  - a drive wheel operably engaged with the piston rod for displacing the piston rod in the distal direction for dose dispensing,
  - wherein the dose indicating member is engageable with the drive wheel during dose dispensing to transfer a driving force to the drive wheel when the dose indicating member is driven by the relaxing spring element in the dose decrementing direction; and
- the cartridge containing the medicament and being arranged in the housing of the drive mechanism.

16. The drug delivery device according to claim 15, wherein the dose indicating member comprises a flat shaped dose indicating disc.

17. The drug delivery device according to claim 15, wherein the spring element comprises a spiral spring having a first end section connected to the housing and having a second end section connected to the dose indicating member.

18. The drug delivery device according to claim 15, further comprising a ring-shaped dose setting member rotatably supported by the housing and being selectively engageable with the dose indicating member for setting of the dose.

19. The drug delivery device according to claim 18, wherein the ring-shaped dose setting member comprises a circumferential side wall portion extending into the housing.

20. The drug delivery device according to claim 19, wherein a last dose limiting member radially sandwiched between the side wall portion and the housing is threadedly engaged with the side wall portion and rotatably locked to the housing.

* * * * *